(12) United States Patent
Kim et al.

(10) Patent No.: US 9,861,793 B2
(45) Date of Patent: Jan. 9, 2018

(54) COREWIRE DESIGN AND CONSTRUCTION FOR MEDICAL DEVICES

(71) Applicant: Acclarent, Inc., Menlo Park, CA (US)

(72) Inventors: Isaac J. Kim, San Jose, CA (US); Ketan P. Muni, San Jose, CA (US)

(73) Assignee: Acclarent, Inc., Irvine, CA (US)

( * ) Notice: Subject to any disclaimer, the term of this patent is extended or adjusted under 35 U.S.C. 154(b) by 0 days.

(21) Appl. No.: 14/699,416

(22) Filed: Apr. 29, 2015

(65) Prior Publication Data

US 2015/0320978 A1 Nov. 12, 2015

Related U.S. Application Data

(63) Continuation of application No. 13/351,774, filed on Jan. 17, 2012, now abandoned, which is a continuation of application No. 12/045,308, filed on Mar. 10, 2008, now Pat. No. 8,182,432.

(51) Int. Cl.
| | |
|---|---|
| *A61M 25/00* | (2006.01) |
| *A61M 25/09* | (2006.01) |
| *A61M 29/02* | (2006.01) |
| *A61B 17/24* | (2006.01) |

(52) U.S. Cl.
CPC ............ *A61M 25/09* (2013.01); *A61M 29/02* (2013.01); *A61B 17/24* (2013.01); *A61M 2025/09083* (2013.01); *A61M 2029/025* (2013.01); *Y10T 29/49908* (2015.01)

(58) Field of Classification Search
CPC ........ A61M 25/09; A61M 2025/09175; A61M 2025/09166; A61M 25/0113
USPC ..................... 600/433, 434, 585; 604/164.13
See application file for complete search history.

(56) References Cited

U.S. PATENT DOCUMENTS

| | | |
|---|---|---|
| 446,173 A | 2/1891 | Hancock |
| 504,424 A | 9/1893 | De Pezzer |
| 513,667 A | 1/1894 | Buckingham |
| 705,346 A | 7/1902 | Hamilton |

(Continued)

FOREIGN PATENT DOCUMENTS

| | | |
|---|---|---|
| CH | 668188 | 12/1988 |
| CN | 2151720 | 1/1994 |
| CN | 2352818 | 12/1999 |
| DE | 3202878 | 8/1983 |
| DE | 4032096 | 4/1992 |
| DE | 4406077 | 9/1994 |

(Continued)

OTHER PUBLICATIONS

U.S. Appl. No. 13/351,774.

(Continued)

*Primary Examiner* — Max Hindenburg
*Assistant Examiner* — Jonathan M Foreman
(74) *Attorney, Agent, or Firm* — Frost Brown Todd LLC

(57) ABSTRACT

A guidewire for use in ear, nose and throat procedures may include an elongate core wire having a proximal region and a distal region. The distal region of the core wire may include a flattened portion adapted to provide preferential flexure along at least one axis of the wire. The distal region of the core wire may include a tip portion distal of the flattened portion, where at least one cross-sectional dimension of the tip portion is greater than at least one cross-sectional dimension of the flattened portion. The guidewire may include an outer coil disposed around at least a portion of the elongate core wire. The guidewire may also include an atraumatic tip coupled to the core wire or the outer coil.

4 Claims, 8 Drawing Sheets

(56) References Cited

U.S. PATENT DOCUMENTS

| | | |
|---|---|---|
| 798,775 A | 9/1905 | Forsyte |
| 816,792 A | 4/1906 | Green |
| 1,080,934 A | 12/1913 | Shackleford |
| 1,200,267 A | 10/1916 | Sunnergren |
| 1,650,959 A | 11/1927 | Pitman |
| 1,735,519 A | 11/1929 | Vance |
| 1,828,986 A | 10/1931 | Stevens |
| 1,878,671 A | 9/1932 | Cantor |
| 2,201,749 A | 5/1940 | Vandegrift |
| 2,493,326 A | 1/1950 | Trinder |
| 2,525,183 A | 10/1950 | Robison |
| 2,847,997 A | 8/1958 | Tibone |
| 2,899,227 A | 8/1959 | Jeanrenaud |
| 2,906,179 A | 9/1959 | Bower |
| 2,995,832 A | 8/1961 | Alderson |
| 3,009,265 A | 11/1961 | Bezark |
| 3,037,286 A | 6/1962 | Bower |
| 3,173,418 A | 3/1965 | Baran |
| 3,347,061 A | 10/1967 | Stuemky |
| 3,376,659 A | 4/1968 | Asin et al. |
| 3,384,970 A | 5/1968 | Avalear |
| 3,393,073 A | 7/1968 | Reutenauer et al. |
| 3,435,826 A | 4/1969 | Fogarty |
| 3,469,578 A | 9/1969 | Bierman |
| 3,481,043 A | 12/1969 | Esch |
| 3,486,539 A | 12/1969 | Jacuzzi |
| 3,506,005 A | 4/1970 | Gilio et al. |
| 3,509,638 A | 5/1970 | Macleod |
| 3,515,888 A | 6/1970 | Lewis |
| 3,527,220 A | 9/1970 | Summers |
| 3,531,868 A | 10/1970 | Stevenson |
| 3,552,384 A | 1/1971 | Pierie et al. |
| 3,624,661 A | 11/1971 | Shebanow |
| 3,731,963 A | 5/1973 | Pond |
| 3,792,391 A | 2/1974 | Ewing |
| 3,800,788 A | 2/1974 | White |
| 3,802,096 A | 4/1974 | Matern |
| 3,804,081 A | 4/1974 | Kinoshita |
| 3,834,394 A | 9/1974 | Hunter et al. |
| 3,850,176 A | 11/1974 | Gottschalk |
| 3,856,000 A | 12/1974 | Chikama |
| 3,859,993 A | 1/1975 | Bitner |
| 3,871,365 A | 3/1975 | Chikama |
| 3,894,538 A | 7/1975 | Richter |
| 3,903,893 A | 9/1975 | Scheer |
| 3,910,617 A | 10/1975 | Scalza et al. |
| 3,921,636 A | 11/1975 | Zaffaroni |
| 3,948,254 A | 4/1976 | Zaffaroni |
| 3,948,262 A | 4/1976 | Zaffaroni |
| 3,967,618 A | 7/1976 | Zaffaroni |
| 3,993,069 A | 11/1976 | Buckles et al. |
| 3,993,072 A | 11/1976 | Zaffaroni |
| 3,993,073 A | 11/1976 | Zaffaroni |
| 4,016,251 A | 4/1977 | Higuchi et al. |
| 4,052,505 A | 10/1977 | Higuchi et al. |
| 4,053,975 A | 10/1977 | Olbrich et al. |
| 4,069,307 A | 1/1978 | Higuchi et al. |
| 4,102,342 A | 7/1978 | Akiyama et al. |
| 4,138,151 A | 2/1979 | Nakao |
| 4,184,497 A | 1/1980 | Kolff et al. |
| 4,198,766 A | 4/1980 | Camin et al. |
| 4,207,890 A | 6/1980 | Mamajek et al. |
| 4,209,919 A | 7/1980 | Kirikae et al. |
| 4,213,095 A | 7/1980 | Falconer |
| 4,217,898 A | 8/1980 | Theeuwes |
| 4,268,115 A | 5/1981 | Slemon et al. |
| 4,299,226 A | 11/1981 | Banka |
| 4,299,227 A | 11/1981 | Lincoff |
| 4,312,353 A | 1/1982 | Shahbabian |
| 4,338,941 A | 7/1982 | Payton |
| D269,204 S | 5/1983 | Trepp |
| 4,388,941 A | 6/1983 | Riedhammer |
| RE31,351 E | 8/1983 | Falconer |
| 4,435,716 A | 3/1984 | Zandbergen |
| 4,437,856 A | 3/1984 | Valli |
| 4,450,150 A | 5/1984 | Sidman |
| 4,459,977 A | 7/1984 | Pizon et al. |
| 4,464,175 A | 8/1984 | Altman et al. |
| 4,471,779 A | 9/1984 | Antoshkiw et al. |
| 4,499,899 A | 2/1985 | Lyons, III |
| 4,554,929 A | 11/1985 | Samson et al. |
| 4,564,364 A | 1/1986 | Zaffaroni et al. |
| 4,571,239 A | 2/1986 | Heyman |
| 4,571,240 A | 2/1986 | Samson et al. |
| 4,581,017 A | 4/1986 | Sahota |
| 4,585,000 A | 4/1986 | Hershenson |
| D283,921 S | 5/1986 | Dyak |
| 4,589,868 A | 5/1986 | Dretler |
| 4,596,528 A | 6/1986 | Lewis et al. |
| D284,892 S | 7/1986 | Glassman |
| 4,603,564 A | 8/1986 | Kleinhany et al. |
| 4,606,346 A | 8/1986 | Berg et al. |
| 4,607,622 A | 8/1986 | Fritch et al. |
| 4,637,389 A | 1/1987 | Heyden |
| 4,639,244 A | 1/1987 | Rizk et al. |
| 4,645,495 A | 2/1987 | Vaillancourt |
| 4,669,469 A | 6/1987 | Gifford, III |
| 4,672,961 A | 6/1987 | Davies |
| 4,675,613 A | 6/1987 | Naegeli et al. |
| 4,691,948 A | 9/1987 | Austin, Jr. et al. |
| 4,708,434 A | 11/1987 | Tsuno |
| 4,708,834 A | 11/1987 | Cohen et al. |
| 4,726,772 A | 2/1988 | Amplatz |
| 4,736,970 A | 4/1988 | McGourty et al. |
| 4,737,141 A | 4/1988 | Spits |
| 4,748,869 A | 6/1988 | Ohtsuka |
| 4,748,969 A | 6/1988 | Wardle |
| 4,748,986 A | 6/1988 | Morrison et al. |
| 4,755,171 A | 7/1988 | Tennant |
| 4,771,776 A | 9/1988 | Powell et al. |
| 4,793,359 A | 12/1988 | Sharrow |
| 4,795,439 A | 1/1989 | Guest |
| 4,796,629 A | 1/1989 | Grayzel |
| 4,803,076 A | 2/1989 | Ranade |
| 4,811,743 A | 3/1989 | Stevens |
| 4,815,478 A | 3/1989 | Buchbinder et al. |
| 4,819,619 A | 4/1989 | Augustine et al. |
| 4,846,186 A | 7/1989 | Box et al. |
| 4,847,258 A | 7/1989 | Sturm et al. |
| 4,851,228 A | 7/1989 | Zentner et al. |
| 4,854,330 A * | 8/1989 | Evans, III ............ A61M 25/09 600/585 |
| 4,862,874 A | 9/1989 | Kellner |
| 4,867,138 A | 9/1989 | Kubota et al. |
| 4,883,465 A | 11/1989 | Brennan |
| 4,897,651 A | 1/1990 | DeMonte |
| 4,898,577 A | 2/1990 | Badger et al. |
| 4,917,419 A | 4/1990 | Mora, Jr. et al. |
| 4,917,667 A | 4/1990 | Jackson |
| 4,919,112 A | 4/1990 | Siegmund |
| 4,920,967 A | 5/1990 | Cottonaro et al. |
| 4,925,445 A | 5/1990 | Sakamoto et al. |
| 4,940,062 A | 7/1990 | Hampton et al. |
| 4,943,275 A | 7/1990 | Stricker |
| 4,946,466 A | 8/1990 | Pinchuk et al. |
| 4,961,433 A | 10/1990 | Christian |
| 4,966,163 A | 10/1990 | Kraus et al. |
| 4,984,581 A | 1/1991 | Stice |
| 4,994,033 A | 2/1991 | Shockey et al. |
| 4,998,916 A | 3/1991 | Hammerslag et al. |
| 4,998,917 A | 3/1991 | Gaiser et al. |
| 5,001,825 A | 3/1991 | Halpern |
| 5,002,322 A | 3/1991 | Fukumoto |
| 5,019,075 A | 5/1991 | Spears et al. |
| 5,019,372 A | 5/1991 | Folkman et al. |
| 5,020,514 A | 6/1991 | Heckele |
| 5,021,043 A | 6/1991 | Becker et al. |
| 5,024,650 A | 6/1991 | Hagiwara et al. |
| 5,024,658 A | 6/1991 | Kozlov et al. |
| 5,026,384 A | 6/1991 | Farr et al. |
| 5,030,227 A | 7/1991 | Rosenbluth et al. |
| 5,041,089 A | 8/1991 | Mueller et al. |
| 5,044,678 A | 9/1991 | Detweiler |
| 5,053,007 A | 10/1991 | Euteneuer |

(56) References Cited

U.S. PATENT DOCUMENTS

| | | |
|---|---|---|
| 5,055,051 A | 10/1991 | Duncan |
| 5,060,660 A | 10/1991 | Gambale et al. |
| 5,067,489 A | 11/1991 | Lind |
| 5,069,226 A | 12/1991 | Yamauchi et al. |
| 5,084,022 A | 1/1992 | Claude |
| 5,087,244 A | 2/1992 | Wolinsky et al. |
| 5,087,246 A | 2/1992 | Smith |
| 5,090,595 A | 2/1992 | Vandeninck |
| 5,090,910 A | 2/1992 | Narlo |
| 5,112,228 A | 5/1992 | Zouras |
| 5,116,311 A | 5/1992 | Lofstedt |
| 5,127,393 A | 7/1992 | McFarlin et al. |
| 5,137,517 A | 8/1992 | Loney et al. |
| 5,139,510 A | 8/1992 | Goldsmith, III et al. |
| 5,139,832 A | 8/1992 | Hayashi et al. |
| D329,496 S | 9/1992 | Wotton |
| 5,152,747 A | 10/1992 | Oliver |
| 5,154,705 A | 10/1992 | Fleischhacker et al. |
| 5,156,595 A | 10/1992 | Adams |
| 5,163,989 A | 11/1992 | Campbell et al. |
| 5,167,220 A | 12/1992 | Brown |
| 5,168,864 A | 12/1992 | Shockey |
| 5,169,386 A | 12/1992 | Becker et al. |
| 5,171,233 A | 12/1992 | Amplatz et al. |
| 5,180,368 A | 1/1993 | Garrison |
| 5,183,470 A | 2/1993 | Wettermann |
| 5,189,110 A | 2/1993 | Ikematu et al. |
| 5,195,168 A | 3/1993 | Yong |
| 5,197,457 A | 3/1993 | Adair |
| 5,207,695 A | 5/1993 | Trout, III |
| 5,211,952 A | 5/1993 | Spicer et al. |
| 5,215,105 A | 6/1993 | Kizelshteyn et al. |
| 5,221,260 A | 6/1993 | Burns et al. |
| 5,226,302 A | 7/1993 | Anderson |
| 5,230,348 A | 7/1993 | Ishibe et al. |
| 5,236,422 A | 8/1993 | Eplett, Jr. |
| 5,243,996 A | 9/1993 | Hall |
| D340,111 S | 10/1993 | Yoshikawa |
| 5,250,059 A | 10/1993 | Andreas et al. |
| 5,251,092 A | 10/1993 | Brady et al. |
| 5,252,183 A | 10/1993 | Shaban et al. |
| 5,255,679 A | 10/1993 | Imran |
| 5,256,144 A | 10/1993 | Kraus et al. |
| 5,263,926 A | 11/1993 | Wilk |
| 5,264,260 A | 11/1993 | Saab |
| 5,267,965 A | 12/1993 | Deneiga |
| 5,270,086 A | 12/1993 | Hamlin |
| 5,273,052 A | 12/1993 | Kraus et al. |
| 5,275,593 A | 1/1994 | Easley et al. |
| 5,286,254 A | 2/1994 | Shapland et al. |
| 5,290,310 A | 3/1994 | Makower et al. |
| 5,295,694 A | 3/1994 | Levin |
| 5,300,085 A | 4/1994 | Yock |
| 5,304,123 A | 4/1994 | Atala et al. |
| 5,308,326 A | 5/1994 | Zimmon |
| 5,313,967 A | 5/1994 | Lieber et al. |
| 5,314,417 A | 5/1994 | Stephens et al. |
| 5,315,618 A | 5/1994 | Yoshida |
| 5,324,306 A | 6/1994 | Makower et al. |
| 5,333,620 A | 8/1994 | Moutafis et al. |
| 5,334,167 A | 8/1994 | Cocanower |
| 5,336,163 A | 8/1994 | DeMane et al. |
| 5,341,818 A | 8/1994 | Abrams et al. |
| 5,342,296 A | 8/1994 | Persson et al. |
| 5,343,865 A | 9/1994 | Gardineer et al. |
| 5,345,945 A | 9/1994 | Hodgson et al. |
| 5,346,075 A | 9/1994 | Nichols et al. |
| 5,346,508 A | 9/1994 | Hastings |
| 5,348,537 A | 9/1994 | Wiesner et al. |
| 5,350,396 A | 9/1994 | Eliachar |
| 5,356,418 A | 10/1994 | Shturman |
| 5,368,049 A | 11/1994 | Raman et al. |
| 5,368,558 A | 11/1994 | Nita |
| 5,368,566 A | 11/1994 | Crocker |
| 5,372,138 A | 12/1994 | Crowley et al. |
| 5,372,584 A | 12/1994 | Zink et al. |
| D355,031 S | 1/1995 | Yoshikawa |
| 5,386,817 A | 2/1995 | Jones |
| 5,391,147 A | 2/1995 | Imran et al. |
| 5,391,179 A | 2/1995 | Mezzoli |
| 5,402,799 A | 4/1995 | Colon et al. |
| 5,409,444 A | 4/1995 | Kensey |
| 5,411,033 A | 5/1995 | Viera |
| 5,411,475 A | 5/1995 | Atala et al. |
| 5,411,476 A | 5/1995 | Abrams et al. |
| 5,411,477 A | 5/1995 | Saab |
| 5,415,633 A | 5/1995 | Lazarus |
| 5,425,370 A | 6/1995 | Vilkomerson |
| 5,439,446 A | 8/1995 | Barry |
| 5,441,494 A | 8/1995 | Ortiz |
| 5,441,497 A | 8/1995 | Narciso, Jr. |
| 5,450,853 A | 9/1995 | Hastings et al. |
| 5,451,221 A | 9/1995 | Cho et al. |
| 5,454,817 A | 10/1995 | Katz |
| 5,458,572 A | 10/1995 | Campbell et al. |
| 5,465,717 A | 11/1995 | Imran et al. |
| 5,465,733 A | 11/1995 | Hinohara et al. |
| 5,478,565 A | 12/1995 | Geria |
| 5,486,181 A | 1/1996 | Cohen et al. |
| 5,496,338 A | 3/1996 | Miyagi et al. |
| 5,497,783 A | 3/1996 | Urick et al. |
| 5,497,786 A * | 3/1996 | Urick .................. A61M 25/09 600/434 |
| 5,507,301 A | 4/1996 | Wasicek et al. |
| 5,507,725 A | 4/1996 | Savage et al. |
| 5,507,766 A | 4/1996 | Kugo et al. |
| 5,512,055 A | 4/1996 | Domb et al. |
| 5,514,128 A | 5/1996 | Hillsman et al. |
| 5,519,532 A | 5/1996 | Broome |
| 5,531,676 A | 7/1996 | Edwards et al. |
| 5,533,985 A | 7/1996 | Wang |
| 5,538,008 A | 7/1996 | Crowe |
| 5,546,964 A | 8/1996 | Stangerup |
| 5,549,542 A | 8/1996 | Kovalcheck |
| 5,558,073 A | 9/1996 | Pomeranz et al. |
| 5,558,652 A | 9/1996 | Henke |
| 5,562,619 A | 10/1996 | Mirarchi et al. |
| 5,568,809 A | 10/1996 | Ben-Haim |
| 5,571,086 A | 11/1996 | Kaplan et al. |
| 5,578,007 A | 11/1996 | Imran |
| 5,578,048 A | 11/1996 | Pasqualucci et al. |
| 5,584,827 A | 12/1996 | Korteweg et al. |
| 5,591,194 A | 1/1997 | Berthiaume |
| 5,599,284 A | 2/1997 | Shea |
| 5,599,304 A | 2/1997 | Shaari |
| 5,599,576 A | 2/1997 | Opolski |
| 5,601,087 A | 2/1997 | Gunderson et al. |
| 5,601,594 A | 2/1997 | Best |
| 5,607,386 A | 3/1997 | Flam |
| 5,617,870 A | 4/1997 | Hastings et al. |
| 5,626,374 A | 5/1997 | Kim |
| 5,633,000 A | 5/1997 | Grossman et al. |
| 5,634,908 A | 6/1997 | Loomas |
| 5,638,819 A | 6/1997 | Manwaring et al. |
| 5,643,251 A | 7/1997 | Hillsman et al. |
| 5,645,789 A | 7/1997 | Roucher, Jr. |
| 5,647,361 A | 7/1997 | Damadian |
| 5,656,030 A | 8/1997 | Hunjan et al. |
| 5,662,674 A | 9/1997 | Debbas |
| 5,664,567 A | 9/1997 | Linder |
| 5,664,580 A | 9/1997 | Erickson et al. |
| 5,665,052 A | 9/1997 | Bullard |
| 5,669,388 A | 9/1997 | Vilkomerson |
| 5,673,707 A | 10/1997 | Chandrasekaran |
| 5,676,673 A | 10/1997 | Ferre et al. |
| 5,679,400 A | 10/1997 | Tuch |
| 5,682,199 A | 10/1997 | Lankford |
| 5,685,838 A | 11/1997 | Peters et al. |
| 5,685,847 A | 11/1997 | Barry |
| 5,690,373 A | 11/1997 | Luker |
| 5,693,065 A | 12/1997 | Rains, III |
| 5,694,945 A | 12/1997 | Ben-Haim |
| 5,697,159 A | 12/1997 | Linden |
| 5,700,286 A | 12/1997 | Tartaglia et al. |

(56) References Cited

U.S. PATENT DOCUMENTS

| | | |
|---|---|---|
| 5,707,389 A | 1/1998 | Louw et al. |
| 5,708,175 A | 1/1998 | Loyanagi et al. |
| 5,711,315 A | 1/1998 | Jerusalmy |
| 5,713,839 A | 2/1998 | Shea |
| 5,713,946 A | 2/1998 | Ben-Haim |
| 5,718,702 A | 2/1998 | Edwards |
| 5,720,300 A | 2/1998 | Fagan et al. |
| 5,722,401 A | 3/1998 | Pietroski et al. |
| 5,722,984 A | 3/1998 | Fischell et al. |
| 5,729,129 A | 3/1998 | Acker |
| 5,730,128 A | 3/1998 | Pomeranz et al. |
| 5,733,248 A | 3/1998 | Adams et al. |
| 5,752,513 A | 5/1998 | Acker et al. |
| 5,762,604 A | 6/1998 | Kieturakis |
| 5,766,158 A | 6/1998 | Opolski |
| 5,775,327 A | 7/1998 | Randolph et al. |
| 5,776,158 A | 7/1998 | Chou |
| 5,779,699 A | 7/1998 | Lipson |
| 5,789,391 A | 8/1998 | Jacobus et al. |
| 5,792,100 A | 8/1998 | Shantha |
| 5,797,878 A | 8/1998 | Bleam |
| 5,803,089 A | 9/1998 | Ferre et al. |
| 5,807,279 A | 9/1998 | Viera |
| 5,814,016 A | 9/1998 | Valley et al. |
| 5,819,723 A | 10/1998 | Joseph |
| 5,820,568 A | 10/1998 | Willis |
| 5,824,044 A | 10/1998 | Quiachon et al. |
| 5,824,048 A | 10/1998 | Tuch |
| 5,824,173 A | 10/1998 | Fontirroche et al. |
| 5,827,224 A | 10/1998 | Shippert |
| 5,830,188 A | 11/1998 | Abouleish |
| 5,833,608 A | 11/1998 | Acker |
| 5,833,645 A | 11/1998 | Lieber et al. |
| 5,833,650 A | 11/1998 | Imran |
| 5,833,682 A | 11/1998 | Amplatz et al. |
| 5,836,638 A | 11/1998 | Slocum |
| 5,836,935 A | 11/1998 | Ashton et al. |
| 5,837,313 A | 11/1998 | Ding et al. |
| 5,843,089 A | 12/1998 | Shatjian et al. |
| 5,843,113 A | 12/1998 | High |
| 5,846,259 A | 12/1998 | Berthiaume |
| 5,857,998 A | 1/1999 | Barry |
| 5,862,693 A | 1/1999 | Myers et al. |
| 5,865,767 A | 2/1999 | Frechette et al. |
| 5,872,879 A | 2/1999 | Hamm |
| 5,873,835 A | 2/1999 | Hastings et al. |
| 5,887,467 A | 3/1999 | Butterweck et al. |
| 5,902,247 A | 5/1999 | Coe et al. |
| 5,902,333 A | 5/1999 | Roberts et al. |
| 5,904,701 A | 5/1999 | Daneshvar |
| 5,908,407 A | 6/1999 | Frazee et al. |
| 5,916,193 A | 6/1999 | Stevens et al. |
| 5,928,192 A | 7/1999 | Maahs |
| 5,931,811 A | 8/1999 | Haissaguerre et al. |
| 5,931,818 A | 8/1999 | Werp et al. |
| 5,932,035 A | 8/1999 | Koger et al. |
| 5,935,061 A | 8/1999 | Acker et al. |
| 5,941,816 A | 8/1999 | Barthel et al. |
| D413,629 S | 9/1999 | Wolff et al. |
| 5,947,988 A | 9/1999 | Smith |
| 5,949,929 A | 9/1999 | Hamm |
| 5,954,693 A | 9/1999 | Barry |
| 5,954,694 A | 9/1999 | Sunseri |
| 5,957,842 A | 9/1999 | Littmann et al. |
| 5,968,085 A | 10/1999 | Morris et al. |
| 5,971,975 A | 10/1999 | Mills et al. |
| 5,979,290 A | 11/1999 | Simeone |
| 5,980,503 A | 11/1999 | Chin |
| 5,980,551 A | 11/1999 | Summers et al. |
| 5,984,945 A | 11/1999 | Sirhan |
| 5,985,307 A | 11/1999 | Hanson et al. |
| 5,997,562 A | 12/1999 | Zadno-Azizi et al. |
| 6,006,126 A | 12/1999 | Cosman |
| 6,006,130 A | 12/1999 | Higo et al. |
| 6,007,516 A | 12/1999 | Burbank et al. |
| 6,007,991 A | 12/1999 | Sivaraman et al. |
| 6,010,511 A | 1/2000 | Murphy |
| 6,013,019 A | 1/2000 | Fischell et al. |
| 6,015,414 A | 1/2000 | Werp et al. |
| 6,016,429 A | 1/2000 | Khafizov et al. |
| 6,016,439 A | 1/2000 | Acker |
| 6,019,736 A | 2/2000 | Avellanet et al. |
| 6,019,777 A | 2/2000 | Mackenzie |
| 6,021,340 A | 2/2000 | Randolph et al. |
| 6,022,313 A | 2/2000 | Ginn et al. |
| 6,027,461 A | 2/2000 | Walker et al. |
| 6,027,478 A | 2/2000 | Katz |
| 6,039,699 A | 3/2000 | Viera |
| 6,042,561 A | 3/2000 | Ash et al. |
| 6,048,299 A | 4/2000 | von Hoffmann |
| 6,048,358 A | 4/2000 | Barak |
| 6,053,172 A | 4/2000 | Hovda et al. |
| 6,056,702 A | 5/2000 | Lorenzo |
| 6,059,752 A | 5/2000 | Segal |
| 6,071,233 A | 6/2000 | Ishikawa et al. |
| 6,079,755 A | 6/2000 | Chang |
| 6,080,190 A | 6/2000 | Schwartz |
| 6,083,148 A | 7/2000 | Williams |
| 6,083,188 A | 7/2000 | Becker et al. |
| 6,086,585 A | 7/2000 | Hovda et al. |
| 6,092,846 A | 7/2000 | Fuss et al. |
| 6,093,150 A | 7/2000 | Chandler et al. |
| 6,093,195 A | 7/2000 | Ouchi |
| 6,109,268 A | 8/2000 | Thapliyal et al. |
| 6,113,567 A | 9/2000 | Becker |
| 6,117,105 A | 9/2000 | Bresnaham et al. |
| 6,122,541 A | 9/2000 | Cosman et al. |
| 6,123,697 A | 9/2000 | Shippert |
| 6,136,006 A | 10/2000 | Johnson et al. |
| 6,139,510 A | 10/2000 | Palermo |
| 6,142,957 A | 11/2000 | Diamond et al. |
| 6,148,823 A | 11/2000 | Hastings |
| 6,149,213 A | 11/2000 | Sokurenko et al. |
| 6,159,170 A | 12/2000 | Borodulin et al. |
| 6,171,298 B1 | 1/2001 | Matsuura et al. |
| 6,171,303 B1 | 1/2001 | Ben-Haim |
| 6,174,280 B1 | 1/2001 | Oneda et al. |
| 6,176,829 B1 | 1/2001 | Vilkomerson |
| 6,179,788 B1 | 1/2001 | Sullivan |
| 6,179,811 B1 | 1/2001 | Fugoso et al. |
| 6,183,461 B1 | 2/2001 | Matsuura et al. |
| 6,183,464 B1 | 2/2001 | Sharp et al. |
| 6,190,353 B1 | 2/2001 | Makower et al. |
| 6,190,381 B1 | 2/2001 | Olsen et al. |
| 6,193,650 B1 | 2/2001 | Ryan, Jr. |
| 6,195,225 B1 | 2/2001 | Komatsu et al. |
| 6,200,257 B1 | 3/2001 | Winkler |
| 6,206,870 B1 | 3/2001 | Kanner |
| 6,213,975 B1 | 4/2001 | Laksin |
| 6,221,042 B1 | 4/2001 | Adams |
| 6,231,543 B1 | 5/2001 | Hedge et al. |
| 6,234,958 B1 | 5/2001 | Snoke et al. |
| 6,238,364 B1 | 5/2001 | Becker |
| 6,238,391 B1 | 5/2001 | Olsen et al. |
| 6,241,519 B1 | 6/2001 | Sedleemayer |
| 6,249,180 B1 | 6/2001 | Maalej et al. |
| 6,254,550 B1 | 7/2001 | McNamara et al. |
| 6,268,574 B1 | 7/2001 | Edens |
| 6,293,957 B1 | 9/2001 | Peters et al. |
| 6,302,875 B1 | 10/2001 | Makower et al. |
| 6,306,105 B1 | 10/2001 | Rooney et al. |
| 6,306,124 B1 | 10/2001 | Jones et al. |
| D450,382 S | 11/2001 | Nestenborg |
| 6,322,495 B1 | 11/2001 | Snow et al. |
| 6,328,564 B1 | 12/2001 | Thurow |
| 6,332,089 B1 | 12/2001 | Acker et al. |
| 6,332,891 B1 | 12/2001 | Himes |
| 6,340,360 B1 | 1/2002 | Lyles et al. |
| 6,348,041 B1 | 2/2002 | Klint |
| 6,352,503 B1 | 3/2002 | Matsui et al. |
| 6,375,615 B1 | 4/2002 | Flaherty et al. |
| 6,375,629 B1 | 4/2002 | Muni et al. |
| 6,383,146 B1 | 5/2002 | Klint |
| 6,386,197 B1 | 5/2002 | Miller |

(56) References Cited

U.S. PATENT DOCUMENTS

| | | |
|---|---|---|
| 6,389,313 B1 | 5/2002 | Marchitto et al. |
| 6,390,993 B1 | 5/2002 | Cornish et al. |
| 6,394,093 B1 | 5/2002 | Lethi |
| 6,398,758 B1 | 6/2002 | Jacobsen et al. |
| 6,409,863 B1 | 6/2002 | Williams et al. |
| 6,419,653 B2 | 7/2002 | Edwards et al. |
| 6,423,012 B1 | 7/2002 | Kato et al. |
| 6,425,877 B1 | 7/2002 | Edwards |
| 6,432,986 B2 | 8/2002 | Levin |
| 6,440,061 B1 | 8/2002 | Wenner et al. |
| 6,443,947 B1 | 9/2002 | Marko et al. |
| 6,445,939 B1 | 9/2002 | Swanson et al. |
| 6,450,975 B1 | 9/2002 | Brennan et al. |
| 6,450,989 B2 | 9/2002 | Dubrul et al. |
| 6,464,650 B2 | 10/2002 | Jafari et al. |
| 6,468,202 B1 | 10/2002 | Irion et al. |
| 6,468,297 B1 | 10/2002 | Williams et al. |
| 6,485,475 B1 | 11/2002 | Chelly |
| 6,491,940 B1 | 12/2002 | Levin |
| 6,494,894 B2 | 12/2002 | Mirarchi |
| 6,500,130 B2 | 12/2002 | Kinsella et al. |
| 6,500,189 B1 | 12/2002 | Lang et al. |
| 6,503,087 B1 | 1/2003 | Eggert et al. |
| 6,503,185 B1 | 1/2003 | Waksman et al. |
| 6,503,263 B2 | 1/2003 | Adams |
| 6,511,418 B2 | 1/2003 | Shahidi et al. |
| 6,514,249 B1 | 2/2003 | Maguire et al. |
| 6,517,478 B2 | 2/2003 | Khadem |
| 6,524,299 B1 | 2/2003 | Tran et al. |
| 6,526,302 B2 | 2/2003 | Hassett |
| 6,527,753 B2 | 3/2003 | Sekine et al. |
| 6,529,756 B1 | 3/2003 | Phan et al. |
| 6,533,754 B1 | 3/2003 | Hisamatsu et al. |
| 6,536,437 B1 | 3/2003 | Dragisic |
| 6,537,294 B1 | 3/2003 | Boyle et al. |
| 6,543,452 B1 | 4/2003 | Lavigne |
| 6,544,230 B1 | 4/2003 | Flaherty et al. |
| 6,549,800 B1 | 4/2003 | Atalar et al. |
| 6,551,239 B2 | 4/2003 | Renner et al. |
| 6,569,146 B1 | 5/2003 | Werner et al. |
| 6,569,147 B1 | 5/2003 | Evans et al. |
| 6,571,131 B1 | 5/2003 | Nguyen |
| 6,572,538 B2 | 6/2003 | Takase |
| 6,572,590 B1 | 6/2003 | Stevens et al. |
| 6,579,285 B2 | 6/2003 | Sinofsky |
| 6,585,639 B1 | 7/2003 | Kotmel et al. |
| 6,585,717 B1 | 7/2003 | Wittenberger et al. |
| 6,585,794 B2 | 7/2003 | Shimoda et al. |
| 6,589,237 B2 | 7/2003 | Woloszko et al. |
| 6,591,130 B2 | 7/2003 | Shahidi |
| 6,596,009 B1 | 7/2003 | Jelic |
| 6,607,546 B1 | 8/2003 | Murken |
| 6,612,999 B2 | 9/2003 | Brennan et al. |
| 6,613,066 B1 | 9/2003 | Fukaya et al. |
| 6,616,601 B2 | 9/2003 | Hayakawa |
| 6,616,659 B1 | 9/2003 | de la Torre et al. |
| 6,616,678 B2 | 9/2003 | Nishtala et al. |
| 6,616,913 B1 | 9/2003 | Mautone |
| 6,619,085 B1 | 9/2003 | Hsieh |
| 6,634,684 B2 | 10/2003 | Spiessl |
| 6,636,758 B2 | 10/2003 | Sanchez et al. |
| 6,638,233 B2 | 10/2003 | Corvi et al. |
| 6,638,268 B2 | 10/2003 | Niazi |
| 6,638,291 B1 | 10/2003 | Ferrera et al. |
| 6,645,193 B2 | 11/2003 | Mangosong |
| 6,652,472 B2 | 11/2003 | Jafari et al. |
| 6,652,480 B1 | 11/2003 | Imran et al. |
| 6,656,166 B2 | 12/2003 | Lurie et al. |
| 6,663,589 B1 | 12/2003 | Halevy |
| 6,669,689 B2 | 12/2003 | Lehmann et al. |
| 6,669,711 B1 | 12/2003 | Noda |
| 6,672,773 B1 | 1/2004 | Glenn et al. |
| 6,673,025 B1 | 1/2004 | Richardson et al. |
| 6,679,871 B2 | 1/2004 | Hahene |
| 6,685,648 B2 | 2/2004 | Flaherty et al. |
| 6,689,096 B1 | 2/2004 | Loubens et al. |
| 6,689,146 B1 | 2/2004 | Himes |
| 6,702,735 B2 | 3/2004 | Kelly |
| 6,712,757 B2 | 3/2004 | Becker et al. |
| 6,714,809 B2 | 3/2004 | Lee et al. |
| 6,716,183 B2 | 4/2004 | Clayman et al. |
| 6,716,216 B1 | 4/2004 | Boucher et al. |
| 6,716,813 B2 | 4/2004 | Lim et al. |
| 6,719,749 B1 | 4/2004 | Schweikert et al. |
| 6,719,763 B2 | 4/2004 | Chung et al. |
| 6,726,701 B2 | 4/2004 | Gilson et al. |
| 6,755,812 B2 | 6/2004 | Peterson et al. |
| 6,776,772 B1 | 8/2004 | de Vrijer et al. |
| 6,780,168 B2 | 8/2004 | Jellie |
| 6,783,522 B2 | 8/2004 | Fischell |
| 6,783,536 B2 | 8/2004 | Vilsmeier et al. |
| 6,786,864 B2 | 9/2004 | Matsuura et al. |
| 6,796,960 B2 | 9/2004 | Cioanta et al. |
| 6,811,544 B2 | 11/2004 | Schaer |
| 6,817,364 B2 | 11/2004 | Garibaldi et al. |
| 6,817,976 B2 | 11/2004 | Rovengo |
| 6,827,683 B2 | 12/2004 | Otawara |
| 6,827,701 B2 | 12/2004 | MacMahon et al. |
| 6,832,715 B2 | 12/2004 | Eungard et al. |
| D501,677 S | 2/2005 | Becker |
| 6,851,290 B1 | 2/2005 | Meier et al. |
| 6,860,264 B2 | 3/2005 | Christopher |
| 6,860,849 B2 | 3/2005 | Matsushita et al. |
| 6,878,106 B1 | 4/2005 | Herrmann |
| 6,890,329 B2 | 5/2005 | Carroll et al. |
| 6,899,672 B2 | 5/2005 | Chin et al. |
| 6,902,556 B2 | 6/2005 | Grimes et al. |
| 6,913,763 B2 | 7/2005 | Lerner |
| 6,927,478 B2 | 8/2005 | Paek |
| 6,939,361 B1 | 9/2005 | Kleshinski |
| 6,939,374 B2 | 9/2005 | Banik et al. |
| 6,955,657 B1 | 10/2005 | Webler |
| 6,966,906 B2 | 11/2005 | Brown |
| 6,971,998 B2 | 12/2005 | Rosenman et al. |
| 6,979,290 B2 | 12/2005 | Mourlas et al. |
| 6,984,203 B2 | 1/2006 | Tartaglia et al. |
| 6,991,597 B2 | 1/2006 | Gellman et al. |
| 6,997,931 B2 | 2/2006 | Sauer et al. |
| 6,997,941 B2 | 2/2006 | Sharkey et al. |
| 7,004,173 B2 | 2/2006 | Sparks et al. |
| 7,008,412 B2 | 3/2006 | Maginot |
| 7,011,654 B2 | 3/2006 | Dubrul et al. |
| 7,022,105 B1 | 4/2006 | Edwards |
| 7,043,961 B2 | 5/2006 | Pandey |
| 7,052,474 B2 | 5/2006 | Castell et al. |
| 7,056,284 B2 | 6/2006 | Martone et al. |
| 7,056,303 B2 | 6/2006 | Dennis et al. |
| 7,074,197 B2 | 7/2006 | Reynolds et al. |
| 7,074,426 B2 | 7/2006 | Kochinke |
| 7,097,612 B2 | 8/2006 | Bertolero et al. |
| 7,108,677 B2 | 9/2006 | Courtney et al. |
| 7,108,706 B2 | 9/2006 | Hogle |
| 7,128,718 B2 | 10/2006 | Hojeibane et al. |
| 7,131,969 B1 | 11/2006 | Hovda et al. |
| 7,140,480 B2 | 11/2006 | Drussel et al. |
| D534,216 S | 12/2006 | Makower et al. |
| 7,160,255 B2 | 1/2007 | Saadat |
| 7,169,140 B1 | 1/2007 | Kume |
| 7,169,163 B2 | 1/2007 | Becker |
| 7,172,562 B2 | 2/2007 | McKinley |
| 7,174,774 B2 | 2/2007 | Pawar et al. |
| 7,182,735 B2 | 2/2007 | Shireman et al. |
| 7,184,827 B1 | 2/2007 | Edwards |
| 7,214,201 B2 | 5/2007 | Burmeister et al. |
| 7,233,820 B2 | 6/2007 | Gilboa |
| 7,235,099 B1 | 6/2007 | Duncavage et al. |
| 7,237,313 B2 | 7/2007 | Skujins et al. |
| 7,252,677 B2 | 8/2007 | Burwell et al. |
| 7,282,057 B2 | 10/2007 | Surti et al. |
| 7,294,345 B2 | 11/2007 | Haapakumpu et al. |
| 7,294,365 B2 | 11/2007 | Hayakawa et al. |
| 7,313,430 B2 | 12/2007 | Urquhart et al. |
| 7,316,168 B2 | 1/2008 | van der Knokke et al. |
| 7,316,656 B2 | 1/2008 | Shireman et al. |

(56) References Cited

U.S. PATENT DOCUMENTS

| | | |
|---|---|---|
| 7,318,831 B2 | 1/2008 | Alvarez et al. |
| 7,322,934 B2 | 1/2008 | Miyake et al. |
| 7,326,235 B2 | 2/2008 | Edwards |
| 7,338,467 B2 | 3/2008 | Lutter |
| 7,343,920 B2 | 3/2008 | Toby et al. |
| 7,359,755 B2 | 4/2008 | Jones et al. |
| 7,361,168 B2 | 4/2008 | Makower et al. |
| 7,366,562 B2 | 4/2008 | Dukesherer |
| 7,371,210 B2 | 5/2008 | Brock et al. |
| 7,381,205 B2 | 6/2008 | Thommen |
| 7,399,283 B2 | 7/2008 | Kato |
| 7,410,480 B2 | 8/2008 | Muni et al. |
| 7,419,497 B2 | 9/2008 | Muni et al. |
| 7,438,701 B2 | 10/2008 | Theeuwes et al. |
| 7,442,191 B2 | 10/2008 | Hovda et al. |
| 7,452,351 B2 | 11/2008 | Miller et al. |
| 7,454,244 B2 | 11/2008 | Kassab et al. |
| 7,455,646 B2 | 11/2008 | Richardson et al. |
| 7,462,175 B2 | 12/2008 | Chang et al. |
| 7,471,994 B2 | 12/2008 | Ford et al. |
| 7,481,218 B2 | 1/2009 | Djupesland |
| 7,481,800 B2 | 1/2009 | Jacques |
| D586,465 S | 2/2009 | Faulkner et al. |
| D586,916 S | 2/2009 | Faulkner et al. |
| 7,488,313 B2 | 2/2009 | Segal et al. |
| 7,488,337 B2 | 2/2009 | Saab et al. |
| 7,493,156 B2 | 2/2009 | Manning et al. |
| 7,500,971 B2 | 3/2009 | Chang et al. |
| D590,502 S | 4/2009 | Geisser et al. |
| 7,520,876 B2 | 4/2009 | Ressemann et al. |
| 7,532,920 B1 | 5/2009 | Ainsworth et al. |
| 7,544,192 B2 | 6/2009 | Eaton et al. |
| 7,559,925 B2 | 7/2009 | Goldfarb et al. |
| 7,610,104 B2 | 10/2009 | Kaplan et al. |
| 7,615,005 B2 | 11/2009 | Stefanchik et al. |
| 7,618,450 B2 | 11/2009 | Zarowski et al. |
| 7,625,335 B2 | 12/2009 | Deichmann et al. |
| 7,632,291 B2 | 12/2009 | Stephens et al. |
| 7,634,233 B2 | 12/2009 | Deng et al. |
| 7,641,644 B2 | 1/2010 | Chang et al. |
| 7,641,668 B2 | 1/2010 | Perry et al. |
| 7,645,272 B2 | 1/2010 | Chang et al. |
| 7,648,367 B1 | 1/2010 | Makower et al. |
| 7,654,997 B2 | 2/2010 | Makower et al. |
| 7,680,244 B2 | 3/2010 | Gertner et al. |
| 7,686,798 B2 | 3/2010 | Eaton et al. |
| 7,691,120 B2 | 4/2010 | Shluzas et al. |
| 7,717,933 B2 | 5/2010 | Becker |
| 7,720,521 B2 | 5/2010 | Chang et al. |
| 7,727,186 B2 | 6/2010 | Makower et al. |
| 7,727,226 B2 | 6/2010 | Chang et al. |
| 7,736,301 B1 | 6/2010 | Webler et al. |
| 7,740,642 B2 | 6/2010 | Becker |
| 7,753,929 B2 | 7/2010 | Becker |
| 7,753,930 B2 | 7/2010 | Becker |
| 7,771,409 B2 | 8/2010 | Chang et al. |
| 7,775,968 B2 | 8/2010 | Mathis |
| 7,799,048 B2 | 9/2010 | Hudson et al. |
| 7,803,150 B2 | 9/2010 | Chang et al. |
| 7,833,282 B2 | 11/2010 | Mandpe |
| 7,837,672 B2 | 11/2010 | Intoccia |
| 7,840,254 B2 | 11/2010 | Glossop |
| 7,854,744 B2 | 12/2010 | Becker |
| D630,321 S | 1/2011 | Hamilton, Jr. |
| 7,875,050 B2 | 1/2011 | Samson et al. |
| D632,791 S | 2/2011 | Murner |
| 7,883,717 B2 | 2/2011 | Varner et al. |
| 7,896,891 B2 | 3/2011 | Catanese, III et al. |
| 7,951,132 B2 | 5/2011 | Eaton et al. |
| 7,988,705 B2 | 8/2011 | Galdonik et al. |
| 7,993,353 B2 | 8/2011 | Rossner et al. |
| 8,002,740 B2 | 8/2011 | Willink et al. |
| 8,014,849 B2 | 9/2011 | Peckham |
| 8,016,752 B2 | 9/2011 | Armstrong et al. |
| 8,025,635 B2 | 9/2011 | Eaton et al. |
| 8,080,000 B2 | 12/2011 | Makower et al. |
| 8,088,063 B2 | 1/2012 | Fujikura et al. |
| 8,088,101 B2 | 1/2012 | Chang et al. |
| 8,090,433 B2 | 1/2012 | Makower et al. |
| 8,100,933 B2 | 1/2012 | Becker |
| 8,104,483 B2 | 1/2012 | Taylor |
| 8,114,062 B2 | 2/2012 | Muni et al. |
| 8,114,113 B2 | 2/2012 | Becker |
| 8,123,722 B2 | 2/2012 | Chang et al. |
| 8,142,422 B2 | 3/2012 | Makower et al. |
| 8,147,545 B2 | 4/2012 | Avior |
| 8,167,821 B2 | 5/2012 | Sharrow |
| 8,182,432 B2 | 5/2012 | Kim et al. |
| 8,190,389 B2 | 5/2012 | Isaac et al. |
| 8,197,433 B2 | 6/2012 | Cohen |
| 8,197,552 B2 | 6/2012 | Mandpe |
| 8,249,700 B2 | 8/2012 | Clifford et al. |
| 8,277,386 B2 | 10/2012 | Ahmed et al. |
| 8,317,816 B2 | 11/2012 | Becker |
| 8,337,454 B2 | 12/2012 | Eaton et al. |
| 8,388,642 B2 | 3/2013 | Muni et al. |
| 8,403,954 B2 | 3/2013 | Santin et al. |
| 8,439,687 B1 | 5/2013 | Morriss et al. |
| 8,535,707 B2 | 9/2013 | Arensdorf et al. |
| 8,585,728 B2 | 11/2013 | Keith et al. |
| 8,585,753 B2 | 11/2013 | Scanlon et al. |
| 8,608,360 B2 | 12/2013 | Nath |
| 8,864,787 B2 | 1/2014 | Muni et al. |
| 8,642,631 B2 | 2/2014 | Anderson et al. |
| 8,715,169 B2 | 5/2014 | Chang et al. |
| 8,718,786 B2 | 5/2014 | Shalev |
| 8,740,929 B2 | 6/2014 | Gopferich et al. |
| 8,747,389 B2 | 6/2014 | Goldfarb et al. |
| 8,764,729 B2 | 7/2014 | Muni et al. |
| 8,828,041 B2 | 9/2014 | Chang et al. |
| 8,858,586 B2 | 10/2014 | Chang et al. |
| 8,858,974 B2 | 10/2014 | Eaton et al. |
| 8,894,614 B2 | 11/2014 | Muni et al. |
| 8,951,225 B2 | 2/2015 | Evard et al. |
| 8,961,398 B2 | 2/2015 | Makower et al. |
| 8,961,495 B2 | 2/2015 | Chang et al. |
| 9,039,657 B2 | 5/2015 | Makower et al. |
| 9,089,258 B2 | 7/2015 | Goldfarb et al. |
| 9,167,961 B2 | 10/2015 | Makower et al. |
| 9,179,823 B2 | 11/2015 | Goldfarb et al. |
| 9,216,112 B2 | 12/2015 | Clifford et al. |
| 9,265,407 B2 | 2/2016 | Goldfarb et al. |
| 9,289,576 B2 | 3/2016 | Mann et al. |
| 9,399,121 B2 | 7/2016 | Goldfarb et al. |
| 9,554,691 B2 | 1/2017 | Goldfarb et al. |
| 9,603,506 B2 | 3/2017 | Goldfarb et al. |
| 2001/0004644 A1 | 6/2001 | Levin |
| 2001/0034530 A1 | 10/2001 | Malackowski et al. |
| 2002/0006961 A1 | 1/2002 | Katz et al. |
| 2002/0055746 A1 | 5/2002 | Burke et al. |
| 2002/0090388 A1 | 7/2002 | Humes et al. |
| 2003/0013985 A1 | 1/2003 | Saadat |
| 2003/0017111 A1 | 1/2003 | Rabito |
| 2003/0018291 A1 | 1/2003 | Hill et al. |
| 2003/0040697 A1 | 2/2003 | Pass et al. |
| 2003/0083608 A1 | 5/2003 | Evans et al. |
| 2003/0114732 A1 | 6/2003 | Webler et al. |
| 2003/0163154 A1 | 8/2003 | Miyata et al. |
| 2004/0015150 A1 | 1/2004 | Zadno-Azizi |
| 2004/0018980 A1 | 1/2004 | Gurney et al. |
| 2004/0034311 A1 | 2/2004 | Mihakcik |
| 2004/0043052 A1 | 3/2004 | Hunter et al. |
| 2004/0058992 A1 | 3/2004 | Marinello et al. |
| 2004/0064105 A1 | 4/2004 | Capes et al. |
| 2004/0127820 A1 | 7/2004 | Clayman et al. |
| 2004/0158229 A1 | 8/2004 | Quinn |
| 2004/0181175 A1 | 9/2004 | Clayman et al. |
| 2004/0193073 A1 | 9/2004 | DeMello et al. |
| 2004/0230156 A1 | 11/2004 | Schreck et al. |
| 2004/0236231 A1 | 11/2004 | Knighton et al. |
| 2004/0249243 A1 | 12/2004 | Kleiner |
| 2004/0267347 A1 | 12/2004 | Cervantes |
| 2005/0027249 A1 | 2/2005 | Reifart et al. |
| 2005/0055077 A1 | 3/2005 | Marco |

(56) References Cited

U.S. PATENT DOCUMENTS

| | | |
|---|---|---|
| 2005/0059931 A1 | 3/2005 | Garrison et al. |
| 2005/0089670 A1 | 4/2005 | Large |
| 2005/0096568 A1* | 5/2005 | Kato ............... A61M 25/09 600/585 |
| 2005/0107738 A1 | 5/2005 | Slater et al. |
| 2005/0113687 A1 | 5/2005 | Herweck et al. |
| 2005/0113850 A1 | 5/2005 | Tagge |
| 2005/0119590 A1 | 6/2005 | Burmeister et al. |
| 2005/0131316 A1 | 6/2005 | Flagle et al. |
| 2005/0143687 A1 | 6/2005 | Rosenblatt et al. |
| 2005/0182319 A1 | 8/2005 | Glossop |
| 2005/0234507 A1 | 10/2005 | Geske et al. |
| 2005/0244472 A1 | 11/2005 | Hughes et al. |
| 2006/0004323 A1 | 1/2006 | Chang et al. |
| 2006/0063973 A1 | 3/2006 | Makower et al. |
| 2006/0173382 A1 | 8/2006 | Schreiner |
| 2006/0190022 A1 | 8/2006 | Beyar et al. |
| 2006/0211752 A1 | 9/2006 | Kohn et al. |
| 2006/0271024 A1 | 11/2006 | Gertner et al. |
| 2007/0020196 A1 | 1/2007 | Pipkin et al. |
| 2007/0060846 A1* | 3/2007 | Hardin ............. A61M 25/09 600/585 |
| 2007/0112358 A1 | 5/2007 | Abbott |
| 2007/0129751 A1* | 6/2007 | Muni ............... A61B 17/24 606/196 |
| 2007/0167682 A1 | 7/2007 | Goldfarb et al. |
| 2007/0208252 A1 | 9/2007 | Makower |
| 2007/0244413 A1* | 10/2007 | Biggins ............ A61M 25/09 600/585 |
| 2007/0249964 A1* | 10/2007 | Richardson ....... A61L 31/10 600/585 |
| 2007/0269385 A1 | 11/2007 | Yun et al. |
| 2007/0293946 A1 | 12/2007 | Gonzales et al. |
| 2008/0033519 A1 | 2/2008 | Burwell et al. |
| 2008/0051804 A1 | 2/2008 | Cottler et al. |
| 2008/0103521 A1 | 5/2008 | Makower et al. |
| 2008/0183128 A1 | 7/2008 | Morriss et al. |
| 2008/0188870 A1 | 8/2008 | Andre et al. |
| 2008/0228085 A1 | 9/2008 | Jenkins et al. |
| 2008/0275483 A1 | 11/2008 | Makower et al. |
| 2008/0319424 A1 | 12/2008 | Muni et al. |
| 2009/0030274 A1 | 1/2009 | Goldfarb et al. |
| 2009/0088728 A1 | 4/2009 | Dollar et al. |
| 2009/0163890 A1 | 6/2009 | Clifford et al. |
| 2009/0187089 A1 | 7/2009 | Say et al. |
| 2009/0187098 A1 | 7/2009 | Makower et al. |
| 2010/0030031 A1 | 2/2010 | Goldfarb et al. |
| 2010/0087811 A1 | 4/2010 | Herrin et al. |
| 2010/0198191 A1 | 8/2010 | Clifford et al. |
| 2010/0274188 A1 | 10/2010 | Chang et al. |
| 2012/0227457 A1 | 9/2012 | Kim et al. |

FOREIGN PATENT DOCUMENTS

| | | |
|---|---|---|
| DE | 8810044 | 11/1998 |
| DE | 29923582 | 12/2000 |
| DE | 10104663 | 8/2002 |
| DE | 10105592 | 8/2002 |
| EP | 129634 | 1/1985 |
| EP | 257605 | 3/1988 |
| EP | 355996 | 2/1990 |
| EP | 418391 | 3/1991 |
| EP | 427852 | 5/1991 |
| EP | 623582 | 11/1994 |
| EP | 624349 | 11/1994 |
| EP | 744400 | 11/1996 |
| EP | 585757 | 6/1997 |
| EP | 893426 | 1/1999 |
| EP | 1042998 | 10/2000 |
| EP | 1166710 | 1/2002 |
| EP | 1413258 | 4/2004 |
| EP | 1944053 | 7/2008 |
| FR | 2859377 | 3/2005 |
| FR | 2916144 | 11/2008 |
| GB | 2125874 | 3/1984 |
| GB | 2305174 | 4/1997 |
| JP | 53-67935 | 6/1978 |
| JP | 10-24098 | 1/1989 |
| JP | 3-503011 | 7/1991 |
| JP | 3-504935 | 10/1991 |
| JP | 4-221313 | 8/1992 |
| JP | 5-211985 | 8/1993 |
| JP | 6-277296 | 10/1994 |
| JP | 7-327916 | 12/1995 |
| JP | 8-317989 | 12/1996 |
| JP | 11-507251 | 6/1999 |
| JP | 2000-501634 | 2/2000 |
| JP | 2001-501846 | 2/2001 |
| JP | 2001-095815 | 4/2001 |
| JP | 2001-526077 | 12/2001 |
| JP | 2002-028166 | 1/2002 |
| JP | 2002-508214 | 3/2002 |
| JP | 2002-537908 | 11/2002 |
| JP | 2002-538850 | 11/2002 |
| JP | 2003-062080 | 3/2003 |
| JP | 2003-521327 | 7/2003 |
| JP | 2004-357728 | 12/2004 |
| JP | 2005-532869 | 11/2005 |
| RU | 2213530 | 10/2003 |
| SU | 1662571 | 7/1991 |
| WO | WO 90/011053 | 10/1990 |
| WO | WO 90/014865 | 12/1990 |
| WO | WO 91/017787 | 11/1991 |
| WO | WO 92/015286 | 9/1992 |
| WO | WO 92/022350 | 12/1992 |
| WO | WO 94/012095 | 6/1994 |
| WO | WO 96/029071 | 9/1996 |
| WO | WO 97/021461 | 6/1997 |
| WO | WO 99/024106 | 5/1999 |
| WO | WO 99/030655 | 6/1999 |
| WO | WO 99/032041 | 7/1999 |
| WO | WO 00/009192 | 2/2000 |
| WO | WO 00/023009 | 4/2000 |
| WO | WO 00/051672 | 9/2000 |
| WO | WO 00/053252 | 9/2000 |
| WO | WO 01/045572 | 6/2001 |
| WO | WO 01/054558 | 8/2001 |
| WO | WO 01/056481 | 8/2001 |
| WO | WO 01/070325 | 9/2001 |
| WO | WO 01/074266 | 10/2001 |
| WO | WO 01/097895 | 12/2001 |
| WO | WO 02/062269 | 8/2002 |
| WO | WO 03/049603 | 6/2003 |
| WO | WO 03/063703 | 8/2003 |
| WO | WO 03/105657 | 12/2003 |
| WO | WO 04/006788 | 1/2004 |
| WO | WO 04/018980 | 3/2004 |
| WO | WO 04/026391 | 4/2004 |
| WO | WO 04/082525 A2 | 9/2004 |
| WO | WO 04/082525 A3 | 9/2004 |
| WO | WO 05/018730 | 3/2005 |
| WO | WO 05/077450 | 8/2005 |
| WO | WO 05/089670 | 9/2005 |
| WO | WO 05/117755 | 12/2005 |
| WO | WO 06/034008 | 3/2006 |
| WO | WO 06/078884 | 7/2006 |
| WO | WO 06/107957 | 10/2006 |
| WO | WO 06/116597 | 11/2006 |
| WO | WO 06/118737 | 11/2006 |
| WO | WO 06/135853 | 12/2006 |
| WO | WO 07/111636 | 10/2007 |
| WO | WO 07/124260 | 11/2007 |
| WO | WO 08/036149 | 3/2008 |
| WO | WO 08/045242 | 4/2008 |
| WO | WO 08/134382 | 5/2008 |
| WO | WO 08/134382 | 11/2008 |

OTHER PUBLICATIONS

Argon Medical. Maxxim Medical. Ad for Sniper Elite™ Hydrophilic Ni—Ti Alloy Guidewire (2001).

(56) References Cited

OTHER PUBLICATIONS

Aust, R., et al. 'The Functional Size of the Human Maxillary Ostium in Vivo' Acta. Otolaryn. (1974) vol. 78 pp. 432-435.
Baim, D.S., MD 'Grossman's Cardiac Catheterization, Angiography, and Intervention' (2000) Lippincott Williams & Wilkins pp. 76, 84 & 214.
Barrett, S. 'Be Wary of Neurocranial Restructuring (NCR)' Chirobase; Jul. 2003; www.chirobase.org/06DD/ncr.html.
Bartal, N. 'An Improved stent for Use in the Surgical Management of Congential Posterior Choanal Atresia' J. Laryngol. Otol (1988) vol. 102 pp. 146-147.
Becker, A.E. 'Restenosis After Angioplasty' The Lancet (1988) vol. 331, No. 8584 p. 532.
Bellis, M., History of the Catheter-Balloon Catheter—Thomas Fogarty, 2006, www.inventors.about.com/library/inventors/blcatheter.htm?p=1.
Benninger et al.; Adult Chronic Rhinosinusitis: Defintions, Diagnosis, Epidemiology, and Pathophysilogy Arch Otolarygol Head and Neck Surg. vol. 129 (Sep. 2003) pp. A1-S32.
Bent et al. 'The Frontal Cell as a Cause of Frontal Sinus Obstruction' American Journal of Rhinology, vol. 8, No. 4 (1994) pp. 185-191.
Binner et al. 'Fibre-Optic Transilunination of the Sinuses: A Comparison of the Value of Radiography and Transillumination in Antral Disease' Clinical Otolaryngology. vol. 3 (1978) pp. 1-11.
Brown, C.L. et al., 'Safety and Feasibility of Balloon Catheter Dilation of Paranasal Sinus Ostia: A Preliminary Investigation' Annals of Otology, Rhinology & Laryngology (2006) vol. 115, No. 4 pp. 293-299.
Casiano et al. 'Endoscopic Lothrop Procedure: the University of Miami Experience' American Journal of Rhinology, vol. 12, No. 5 (1998) pp. 335-339.
Casserly, I.P. et al., Chapter 7. 'Guides and Wires in Percutaneous Coronary Intervention' Strategic Approaches in Coronary Intervention (2006) Lippincott Williams & Wilkins pp. 91-99.
Chien, Y.W. et al. 'Nasal Systemic Drug Delivery' Drugs and Pharmaceutical Sciences, vol. 39, 1989, pp. 60-63.
Cohen et al. 'Endoscopic Sinus Surgery: Wherre we are and where we're going' Current Opinion in Otolaryngology & Head and Neck Surgery, vol. 13 (2005) pp. 32-38.
Colla, A. et al., 'Trihaloacetylated Enol Ethers—General Synthetic Procedure and Heterocyclic Ring Closure Reactions with Hydroxylamine' Synthesis, (Jun. 1991) pp. 483-486.
Costa, M.N. et al. 'Endoscopic Study of the Intranasal Ostium in External Dacryocystorhinostomy Postoperative Influence of Saline Solution and 5-Flurorouracil' Clinics (2007) vol. 62, Issue1, pp. 41-46.
Cussler, E.L. 'Diffusion: Mass transfer in Fluid Systems' Cambridge University Press (1996).
Davis, G.E. et al. 'A Complication from Neurocranial Restructuring' Arch Otolaryngol Head Neck Surg. vol. 129 (Apr. 2003) pp. 472-474.
Deutschmann, R. et al. 'A Contribution to the Topical Treatment of [Maxillary] Sinusitis Preliminary Communication' Stomat DDR 26, (1976) pp. 585-592.
Domb, A. et al. 'Handbook of Biodegradable Polymers' Hardwood Academic Publishers (1997).
Doyle Nasal Splints, Jan. 25, 2007; www.doylemedical.com/nasalsplints.htm.
Draf, W. 'Endonasal Micro-Endoscopic Frontal Sinus Surgery: the Fulda Concept' Op Tech Otolaryngol Head Neck Surg. vol. 2 (1991) pp. 234-240.
Edmond, C. et al. 'ENT Surgical Stimulator' Nov. 1989.
ENT Checklist; Physical Examination Performance Checklist [date of publication unknown].
Eremychev, V.A. 'Needles for Puncture and Drainage of the Maxillary Sinus' Meditsinskaya Tekhnika, No. 5 (1974) pp. 54.55.
Feldman, R.L. et al., 'New Steerable, Ultra-Low-Profile, Fixed Wire Angioplasty Catheter: Initial Experience With the Cordis OrionTM Steerable PTCA Balloon Catheter' Cathet. Cardiovasc. Diagn. (1990) vol. 19, No. 2 pp. 142-145.
Ford, C.N. 'A Multipurpose Laryngeal Injector Device' Otolaryngol. Head Neck Surg. (1990) vol. 103, No. 1 pp. 135-137.
Friedman, et al 'Middle Turbinate Medialization and Preservation in Endoscopic Surgery' Otolaryngology—Head and Neck Surgery. (2000) vol. 123, No. 1, part 1, pp. 76-80.
Friedman, et al. 'Intraoperative and Postoperative Assessment of Frontal Sinus Patency by Transillumination' Laryngoscope. vol. 110 (Apr. 2000) pp. 683-684.
Friedman, M., M.D., et al. 'Frontal Sinus Surgery: Endoscopic Technique' Operative Techniques in Otolarynology—Head and Neck Surgery. vol. 12, No. 2 (Jun. 2001) pp. 60-65.
Fung, M.K.T. 'Template for Frontal Osteoplastic Flap' Laryngoscope. vol. 96 (1986) pp. 578-579.
Gatot, A. et al. 'Early treatment of Orbital Floor Fractures with Catheter Balloon in Children' Int J. Pediatric Otorhinolaryngol (1991) vol. 21 pp. 97-101.
Gerus, I.I. et al. 'β-Ethoxyvinyl Polyfluroroalkyl Ketones—Versatile Synthones in Fluoroorganic Chemistry' Journal of Fluorine Chemistry. vol. 69 (1994) pp. 195-198. Elesvier Science S.A.
Good, R.H. 'An Intranasal Method for Opening the Frontal Sinus Establishing the Largest Possible Drainage' Laryngoscope. vol. 18 (1908) pp. 266-274.
Gopferich 'Polymer Degradation and Erosion: Mechanisms and Application' Eur. J. Parm. Biophar. vol. 42 (1996) pp. 1-11.
Gorlov, D.V. et al 'Acylation of 2-Methoxypropene with Anhydrides and Halides of Perflurocarboxylic Acids in the Presence of Teriary Amines' Russian Chemical Bulletin. vol. 48 No. 9 (Sep. 1999) pp. 1791-1792. Kluwer Academic/Plenum Publishers.
Gottmann, et al. 'Balloon Dilatation of Recurrent Ostial Occlusion of the Frontal Sinus' CIRSE Abstract (Mar. 2001) B-04353.
Gottmann, et al. 'Balloon Dilatation in the Nasal Cavity and Paranasal Sinuses' CIRSE. (Sep. 25, 2004) pp. 1-27.
Gottmann, et al. 'Successful Treatment of Recurrent Post-Operative Frontal Sinus Stenoses by Balloon Dilatation' CIRSE. (Oct. 5, 2002).
Gupta, D. et al., 'Dacrystitis Secondary to an Iatrogenic Foreign Body in the Lacrimal Apparatus' Ear, Nose & Throat Journal (2009) www.findarticles.com/p/articles/mi_m0BUM/is_7_88/ai_n32428620/.
Hashim, et al. 'Balloon Compression of the Intermaxillary Sinus for Intractable Post Traumatic Bleeding from the Maxillary Artery' Scandinavian Journal of Plastic and reconstruction Sergery and Hand Surgery (1999) vol. 33 pp. 321-324.
Hojo, M. et al, 'Electrophilic Substiutions of Olefinic Hydrogens II. Acylation of Vinyle Ethers and N Vinyl Amides Chemistry Letters' (1976) pp. 499-502. Chemical Society of Japan.
Hopf, J.U.G. et al. 'Minature Endoscopes in Otorhinolaryngologic Applications' Min Invas Ther & Allied Technol. (1998) vol. 7, No. 3 pp. 209-218.
Hosemann, M.E. et al. 'Experimentelle Untersuchungen sur Wundheilung in den Nasennebenholhlen. II. Spontaner Wundschluss and medikamentose Effekte im standardisierten Wundmodell.' HNO 39 (1991) pp. 48-54.
Hosemann, M.E. et al. 'Normal Wound Healing of the Paranasal Sinuses—Clinical and Experimental Investigations' Eur Arch Otorhinolarygol. vol. 248, (1991) pp. 390-394.
Hosemann, W. et al. 'A Dissection Course on Endoscopic Endonasal Sinus Surgery (2005) Endo-Press, Tuttlingen pp. 4-37.
Hosemann, W. et al. 'Behandlung nach Nasennebenhohleneingriffen, part 2: Theapeutische Maβnahem' HNO akutell 7 (1999) pp. 291-302.
Hosemann, W. et al. 'Endonasal Frontal Sinusotomy in Surgical Management of Chronic Sinusitis: A Critical Evaluation' American Journal of Rhinology. vol. 11, No. 1 (1997) pp. 1-9.
Hosemann, W.G. et al. 'Minimally Invasive Endonasal Sinus Surgery' Thieme, Stuttgart, New York (2000).
Hospital Corpsman Sickcall Screener's Handbook. Naval Hospital Great Lakes (Apr. 1999) www.brooksidepress.org/Products/Operationa.Medicine/DATA. 2001 pp. 1-6.
Hybels, R.L. 'Transillumination Durning Osteoplastic Frontal Sinusotomy' The Laryngoscope. vol. 91 (Sep. 1981) pp. 1560.

(56) References Cited

OTHER PUBLICATIONS

Ijaduola, T.G.A. 'Use of a Foley Catheter for Short-Term Drainage in Frontal Sinus Surgery' Ther Journal of Laryngology and Otology. (1989) vol. 103. pp. 375.378.
Ingals, E.F. 'New Operation and Instruments for Draining the Frontal Sinus' Ann. Otol. Rhinol. Layyngol. vol. 14 (1905) pp. 644-649.
Iro, H. et al., 'A New Device for Frontal Sinus Endoscopy: First Clinical Report' Otolaryngol. Head Neck Surg. (2001) vol. 125 No. 6 pp. 613-616.
Jacobs, J.B. '100 Years of Frontal Sinus Surgery' Laryngoscope. vol. 107 (1997) pp. 1-36.
K-Splint Internal Nasal Splints; Jan. 25, 2007; www.invotec.net/rhinology/ksplint.html.
Kaiser, H. et al 'Cortizontherapie, Corticoide in Klinik und Praxis' Thieme, Stuggart (1992) pp. 390-401.
Kennedy, D.W., M.D. et al. 'Diseases of the Sinuses: Diagnosis and Management' (Copyright 2001) by B.C. Decker Inc.
Khomutov, S.M. et al. 'Dissolution of a Mixture of Steroids in Cyclodextrin Solutions: A Model Description' Pharmaceutical Chemistry Journal. vol. 35, No. 11 (Nov. 2001) pp. 627-629.
Kingdom, T.T. et al. 'Image-Guided Surgery of the Sinuses: Current Technology and Applications' Otolaryngol. Clin. North Am. vol. 37, No. 2 (Apr. 2004) pp. 381-400.
Klossek, J.M. et al. 'Local Safety of Intranasal Trimcinolone Acentonide: Clinical and Histological Aspects of Nasal Mucosa in the Long-Term Treatment of Perennial Allergic Rhinitis' Rhinology. vol. 39, No. 1 (2001) pp. 17-22.
Kozlov et al. 'Diagnosis and Treatment of Sinusitis by YAMIK Sinus Catheters' Rhinology (1996) vol. 34, pp. 123-124.
Kuhn, et al. 'The Agger Nasi Cell in Frontal Recess Obstruction: An Anatomic, Radiology and Clinical Correlation' Operative Techniques in Otolaryngology—Head and Neck Surgery. vol. 2, No. 4 (1991) pp. 226-231.
Laliberte, F. et al. 'Clinical and Pathologic Methods to Assess the Long-Term Safety of Nasal Corticosteroids' Allergy. vol. 55, No. 8 (2000) pp. 718-722.
Lang, E.V., et al., 'Access Systems for Puncture at an Acute Angle' J. Vasc. Interv. Radiol. (1995) vol. 6, No. 5 pp. 711-713.
Lanza, D.C. 'Postoperative Care and Avoiding Frontal Recess Stenosis' Internatinal Advanced Sinus Symposium (1993) Jul. 21-24.
Large, G.C. 'Crystalline Tetracycline Hydrochloride in the Treatment of Acute and Chronic Maxillary Sinusitis' Canad. M.A.J. (1958) vol. 79 pp. 15-16.
Lund, V.J. 'Maximal Medical Therapy for Chronic Rhinosinusitis' Otolaryngol Clin N. Am. vol. 38 (2005) pp. 1301-1310.
Maran, A.G.D. et al. 'The Use of the Foley Balloon Catheter in the Tripod Fracture' J. Laryngol. Otol. (1971) vol. 85, Issue 9, pp. 897-902.
May, M. et al. 'Frontal Sinus Surgery: Endonasal Drainage Instead of an External Osteopolstic Approach' Op Tech Otolaryngo Head Neck Surgery. 6 (1995) pp. 184-192.
Medtronic, xomed.com—MicroFrance Catalog Browser, Www.xomcat.com/xomfrance/index.php?zone=both&cat=18&sub=58&prodline=1272 (Dec. 31, 2003) pp. 1-2.
Mehan, V.K. et al., 'Coronary Angioplasty through 4 French Diagnostic Cathers' Cathet. Cardiovasc. Diagn. (1993) vol. 30, No. 1, pp. 22-26.
Mellor, J.M. et al 'Synthesis of Trifluromethylnaphthalenes' Tetrahedron. vol. 56 (2000) pp. 10067-10074. Elsevier Science Ltd.
Metson, R. 'Holmium: YAG Laser Endoscopic Sinus Surgery: A Randomized Controlled Study' Laryngoscope. vol. 106, Issue 1, Supplement 77 (Jan. 1996) pp. 1-18.
Metson, R., et al., 'Endoscopic Treatment of Sphenoid Sinusitis' Otolaryngol. Head Neck Surg. (1996) vol. 114, No. 6 pp. 763-744.
Miller, et al. 'Management of Fractures of the Supraorbital Rim' Journal of Trauma. vol. 18, No. 7 (Jul. 1978) pp. 507-512.
Min, Y-G et al. 'Mucociliary Activity and Histopathology of Sinus Mucosa in Experimental Maxilary Sinusitis: A Comparison of Systemic Administration of Antibiotic and Antibiotic Delivery by Polylactic Acid Polymer' Laryngoscope. vol. 105 (Aug. 1995) pp. 835-842.
Mols, B. 'Movable Tool Tip for Keyhole Surgery' Delft Outlook, vol. 3 (2005) pp. 13-17.
Mooney, M.R., et al., 'Monorail™ Piccolino Catheter: A New Rapid Exchange/Ultralow Profile Coronary Angioplasty System' Cathet. Cardiovasc. Diagn. (1990) vol. 20, No. 2 pp. 114-119.
Moriguchi, T. et al. 'Additional-Elimination Reaction in the Trifluoroacetylation of Electron-Rich Olefins' J. Org. Chem. vol. 60, No. 11 (1995) pp. 3523.3528. American Chemical Society.
Nasal Surgery and Accessories, Jan. 25, 2007; www.technologyforlife.com.au/ent/nasal.html.
Park, K. et al. 'Biodegradable Hydrogels for Durg Delivery' (1993) Technomic Publishing Publishing Inc. Lancaster.
Piccirillo, J.F. et al. 'Physchometric and Clinimetric Validity of the 20-Item Sino-Nasal Outcome test (SNOT-20)' Copyright 1996 Washington University, St. Louis, MO.
Piers, et al. 'A Flexible Distal Tip with Two Degrees of Freedom for Enhanced Dexterity in Endoscopic Robot Surgery' Proceedings 13th Micromechanics Europe Workshop (2002) pp. 271-274.
Podoshin, L et al. 'Balloon Technique for Treatment of Frontal Sinus Fractures' The journal of Laryngology & Otology (1967), vol. 81. pp. 1157-1161.
Pownell, P.H. et al., 'Diagnostic Nasal Endoscopy' plastic & Reconstructive Surgery (1997) vol. 99, Iss5 pp. 1451-1458.
Prince, et al. 'Analysis of the Intranasal Distribution of Ointment' J Otolaryngol. vol. 26 (1997) pp. 357-360.
Ramsdale, D.R., Illustrated Coronary Intervention: A case-oriented approach, (2001) Martin Dunitz Ltd. pp. 1-5.
Ritter, F.N. et al., Atlas of Paranasal Sinus Surgery (1991) Igaku-Shoin Medical Pub. pp. 1-81.
Robison, J. Mathews, M.D. 'Pressure Treatment of Maxillary Sinusitis' J.A.M.A. (May 31, 1952) pp. 436-440.
Robison, J. Mathews, M.D. 'Pressure Treatment of Purulent Maxillary Sinusitis' Texas State Journal of Medicine (May 1952) pp. 281-288.
Sama, A., et al., 'Current Opinions on the Surgical Management of Frontal Sinus Disease' ENT News. Www.pinpointmedical.com/ent-news (2009) vol. 17, No. 6 pp. 60-63.
Sanborn, T.A. et al., 'Percutaneous Endocardial Transfer and Expression of Genes to the Myocardium Utilizing Fluropscopic Guidance' Catheter Cardiovasc. Interv. (2001) vol. 52, No. 2 pp. 260-266.
Sawbones Catalog 2001, Pacific Research Laboratories, Inc., Vashon Washington 98070 USA.
Saxon, R.R. et al., 'Technical Aspects of Accessing the Portal Vein During the TIPS Procedure' J. Vasc. Interv. Radiol. (1997) vol. 8, No. 5 pp. 733-744.
Schaefer, S.D., M.D. 'Rhinology and Sinus Disease: A Problem-Oriented Approach' (Copyright 1988) by Mosby, Inc.
Schneider. Pfizer Ad for Softip [date of publication unknown].
Shah, N.J. et al., 'Endoscopic Pituitary Surgery—A Beginner's Guide' Indian Journal of Otolaryngology and Head and Neck Surgery (2004) vol. 56, No. 1 pp. 71-78.
Shah, N.J. 'Functional Endoscopic Sinus Surgery' (1999); found at bhj.org/journal/1999_4104_oct99/sp_659.htm.
Single-Pole and Multi-Pole Lightguides for UV Spot Light Curing Systems, www.dymax.com/products/curing_equipment/lightguids/light, 2004, pp. 1-2.
Sobol, et al. 'Sinusitis, Maxillary, Acute Surgical Treatment.' eMedicine. Retrieved from the Internet: <<http://emedicine.medscape.com/article/862030-print>> (Nov. 16, 2010) pp. 1-11.
St. Croix et al. 'Genes Expressed in Human Tumor Endothelium' Science, vol. 289 (May 15, 2000) pp. 1197-1202.
Stammberger, et al. Chapter 3 'Special Endoscopic Anatomy of the Lateral Nasal Wall and Ethmoidal Sinuses' Functional Endoscopic Sinus Surgery. (1991) Ch. 3, pp. 49-87.
Stammberger, H. 'Komplikationen entzundlicher Nasennebenhohlenerkrankungen eischließ iatrogen bedingter Komplikationen' Eur Arch Oti-Rhino-Laryngol Supple. (Jan. 1993) pp. 61-102.

(56) References Cited

OTHER PUBLICATIONS

Strohm, et al 'Le Traitenment Des Stenoses Voies Aeriennes Superieures Par Dilation Ay Balloon' Sep. 25, 1999.
Strohm, et al. Die Behandlung von Stenosen der oberen Luftwege mittels rontgenologisch gesteuerter Ballondilation (Sep. 25, 1999) pp. 1-4.
Strohm, et al. 'Treatment of Stenoses of the Upper Airways by Balloon Dilation' Sudwestdeutscher Abstract 45 (Sep. 25, 1999) pp. 1-3.
SurgTrainer Product Information 'Incisive Human Nasal Model for ESS Training' Surg Trainer, Ltd. Ibaraki, Japan (2004) www1.accsnet.ne.jp/~juliy/st/en/partslist.html.
Tabor, M.H. et al., 'Symptomatic Bilateral Duct Cysts in a Newborn—Rhinoscopic Clinic' Ear, Nose & Throat Journal (2003) www.findarticles.com/p/articles/mi_m0BUM/is_2_82/ai_98248244 pp. 1-3.
Tarasov, D.I. et al. 'Application of Drugs Based on Polymers in the Treatment of Acute and Chronic Maxillary Sinusitis' Vestn Otorinoloaringol. vol. 6 (1978) pp. 45-47.
Terumo. Medi-Tech. Boston Scientific. (1993) Ad of Glidewire.
The Operating Theatre Journal (www.otjonline.com) 'Disposable Medical Device for Wound Disclosure/The Tristel Purple Promotion—A Collaboration between Tristel PLC and Karl Storz Endoscopy (UK) Ltd.' 2005, p. 4.
Weber, R. et al. 'Endonasale Stirnhohlenchirugie mit Langzeiteinlage eines Platzhalters' Laryngol. Rhinol. Otol. vol. 76 (1997) pp. 728-734. (English Abstract).
Weber, R. et al., 'Videoendoscopic Analysis of Nasal Steriod Distribution' Rhinology. vol. 37 (1999) pp. 69-73.
Weiner, R.I., D.O., et al., 'Development and Application of Transseptal Left Heart Catheterization' Cathet. Cardiovasc. Diagn. (1988) vol. 15, No. 2, pp. 112-120.
Wiatrak, B.J., et al., 'Unilateral Choanal Atresia: Initial Presentation and Endoscopic Repair' International Journal of Pediatric Otorhinolaryngology (1998) vol. 46, pp. 27-35.
Woog, et al. 'Paranasal Sinus Endoscopy and Orbital Fracture Repair' Arch Ophthalmol. vol. 116 (May 1998) pp. 688-691.
Wormald, P.J., et al., 'The 'Swing-Door'Technique for Uncinectomy in Endoscopic Sinus Surgery' The Journal of Laryngology and Otology (1998) vol. 112, pp. 547-551.
Xomed-Treace. Bristol-Myers Squibb. Ad for Laser Shield II. Setting the Standards for Tomorrow. [date of publication unknown].
Yamauchi, Y. et al., 'Development of a Silicone Model for Endoscopic Sinus Surgery' Proc International Journal of Computer Assisted Radiology and Surgery vol. 99 (1999) p. 1039.
Yamauchi, Y., et al., 'A Training System for Endoscopic Sinus Surgery with Skill Evaluation' Computer Assisted Radiology and Surgery (2001) with accompanying poster presentation.
Yanagisawa et al. 'Anterior and Posterior Fontanelles.' Ear, Nose & Throat Journal (2001) vol. 80. pp. 10-12.
Zimarino, M., M.D., et al., 'Initial Experience with the EuropassTM: A new Ultra-Low Profile monorail Balloon Catheter' Cathet. Cardiovasc. Diagn. (1994) vol. 33, No. 1, pp. 76-79.
Australian Office Action, Examiners First Report dated Apr. 8, 2010 for Application No. AU 2005274794.
European Communication dated Sep. 4, 2008 for Application No. EP 05773189.
European Communication dated Jun. 19, 2009 for Application No. EP 05773189.
European Exam Report dated Feb. 22, 2006 for Application No. EP 02716734.5.
European Exam Report dated Feb. 8, 2007 for Application No. EP 02716734.5.
European Search Report and Written Opinion dated Sep. 11, 2009 for Application No. EP 06815174.
European Search Report dated Sep. 27, 2011 for Application No. EP 10182961.
European Search Report dated Sep. 29, 2011 for Application No. EP 10182893.
Partial European Search Report dated Mar. 25, 2008 for Application No. EP 07252018.
Partial European Search Report dated Sep. 20, 2007 for Application No. EP 07252018.
Supplemental European Search Report dated Jan. 29, 2010 for Application No. EP 07836108.
Supplemental European Search Report dated Feb. 2, 2010 for Application No. EP 07836109.
Supplemental European Search Report dated Feb. 17, 2010 for Application No. EP 07836110.
Supplemental European Search Report dated Mar. 1, 2010 for Application No. EP 05778834.
Supplemental European Search Report dated Mar. 16, 2010 for Application No. EP 06718986.
Supplemental European Search Report dated Jun. 22, 2010 for Application No. EP 06784759.
Supplemental European Search Report dated Sep. 23, 2010 for Application No. EP 08746715.
Supplemental European Search Report dated Jan. 28, 2011 for Application No. EP 07777004.
Supplemental European Search Report dated Mar. 31, 2011 for Application No. EP 06800540.
Supplemental European Search Report dated Aug. 30, 2011 for Application No. EP 06800540.
Supplemental European Search Report dated Sep. 29, 2011 for Application No. EP 07750248.
Supplemental Partial European Search Report dated Jun. 2, 2008 for Application No. EP 05773189.
Supplemental Partial European Search Report dated Jul. 1, 2009 for Application No. EP 06815285.
Supplemental Partial European Search Report dated Nov. 19, 2010 for Application No. EP 06751637.
International Search Report and Written Opinion dated Apr. 10, 2006 for Application No. PCT/US2005/25371.
International Preliminary Report on Patentability dated Aug. 7, 2006 for Application No. PCT/US2005/25371.
International Search Report and Written Opinion dated Jul. 21, 2008 for Application No. PCT/US2005/033090.
International Search Report and Written Opinion dated Sep. 12, 2008 for Application No. PCT/US2007/16214.
International Search Report and Written Opinion dated Sep. 17, 2008 for Application No. PCT/US2008/059786.
International Preliminary Report on Patentability and Written Opinion dated Oct. 13, 2009 for Application No. PCT/US2008/059786.
International Search Report and Written Opinion dated Sep. 17, 2008 for Application No. PCT/US2008/061343.
International Preliminary Report on Patentability and Written Opinion dated Oct. 27, 2009 for Application No. PCT/US2008/061343.
International Search Report and Written Opinion dated Oct. 1, 2008 for Application No. PCT/US2007/011449.
International Preliminary Report on Patentability and Written Opinion dated Nov. 18, 2008 for Application No. PCT/US2007/11449.
International Search Report and Written Opinion dated Oct. 6, 2010 for Application No. PCT/US2010/040548.
International Search Report dated Jun. 3, 2002 for Application No. PCT/EP2002/01228.
International Search Report dated May 8, 2007 for Application No. PCT/US2006/16026.
International Search Report dated Aug. 17, 2007 for Application No. PCT/US2005/013617.
International Search Report dated Aug. 29, 2007 for Application No. PCT/US2006/002004.
International Preliminary Report on Patentability and Written Opinion dated Sep. 25, 2007 for Application No. PCT/US2006/002004.
International Search Report dated Sep. 25, 2007 for Application No. PCT/US2006/037167.
International Search Report dated Oct. 19, 2007 for Application No. PCT/US2007/003394.
International Search Report dated May 29, 2008 for Application No. PCT/US2007/021170.
International Preliminary Report on Patentability and Written Opinion dated Apr. 7, 2009 for Application No. PCT/2007/021170.

(56) References Cited

OTHER PUBLICATIONS

International Search Report dated May 29, 2008 for Application No. PCT/US2007/021922.
International Search Report and Written Opinion dated Jul. 1, 2008 for Application No. PCT/US2006/022745.
International Search Report dated Jul. 3, 2008 for Application No. PCT/US2006/029695.
International Search Report dated Jul. 7, 2008 for Application No. PCT/US2007/016213.
International Search Report dated Jul. 8, 2008 for Application No. PCT/US2007/011474.
International Search Report dated Jul. 17, 2008 for Application No. PCT/US2006/036960.
International Preliminary Report on Patentability and Written Opinion dated May 5, 2009 for Application No. PCT/US2006/036960.
International Search Report dated Aug. 25, 2008 for Application No. PCT/US2008/000911.
International Search Report dated Sep. 10, 2008 for Application No. PCT/US2007/016212.
International Search Report dated Oct. 15, 2008 for Application No. PCT/US2008/061048.
International Search Report dated Nov. 30, 2009 for Application No. PCT/US2009/057203.
International Search Report dated Dec. 10, 2009 for Application No. PCT/US2009/052236.
International Search Report dated Dec. 16, 2009 for Application No. PCT/US2009/050800.
International Search Report dated Mar. 31, 2010 for Application No. PCT/US2009/069143.
International Search Report dated Jul. 8, 2010 for Application No. PCT/US2010/027837.
International Search Report dated Mar. 25, 2011 for Application No. PCT/US2010/062161.
International Search Report dated Mar. 28, 2011 for Application No. PCT/US2010/061850.
International Search Report dated Mar. 31, 2011 for Application No. PCT/US2010/060898.
International Search Report dated Aug. 9, 2011 for Application No. PCT/US2011/038751.
International Search Report dated May 18, 2012 for Application No. PCT/US2011/052321.
Partial International Search Report dated Feb. 7, 2012 for Application No. PCT/US2011/052321.
USPTO Office Action dated Sep. 16, 2005 for U.S. Appl. No. 10/259,300.
USPTO Office Action dated Jul. 7, 2006 for U.S. Appl. No. 10/259,300.
USPTO Office Action dated Feb. 13, 2007 for U.S. Appl. No. 10/259,300.
USPTO Office Action dated Oct. 9, 2007 for U.S. Appl. No. 10/259,300.
USPTO Office Action dated Jan. 24, 2008 for U.S. Appl. No. 10/259,300.
USPTO Office Action dated Oct. 6, 2008 for U.S. Appl. No. 10/259,300.
USPTO Office Action dated May 29, 2007 for U.S. Appl. No. 10/912,578.
USPTO Office Action dated Nov. 14, 2007 for U.S. Appl. No. US 10/912,578.
USPTO Office Action dated Dec. 10, 2007 for U.S. Appl. No. US 10/912,578.
USPTO Office Action dated Oct. 18, 2007 for U.S. Appl. No. 11/037,548.
USPTO Office Action dated Dec. 6, 2007 for U.S. Appl. No. 11/037,548.
USPTO Office Action dated Apr. 9, 2008 for U.S. Appl. No. 11/037,548.
USPTO Office Action dated Nov. 28, 2007 for U.S. Appl. No. 11/234,395.
USPTO Office Action dated Sep. 12, 2008 for U.S. Appl. No. 10/829,917.
USPTO Office Action dated Nov. 17, 2008 for U.S. Appl. No. 10/829,917.
USPTO Office Action dated Mar. 18, 2009 for U.S. Appl. No. 10/829,917.
USPTO Office Action dated Nov. 9, 2009 for U.S. Appl. No. 10/829,917.
USPTO Office Action dated Oct. 29, 2008 for U.S. Appl. No. 11/347,147.
USPTO Office Action dated Feb. 4, 2009 for U.S. Appl. No. 11/347,147.
USPTO Office Action dated Aug. 6, 2009 for U.S. Appl. No. 11/347,147.
USPTO Office Action dated Nov. 7, 2008 for U.S. Appl. No. 10/944,270.
USPTO Office Action dated Jan. 28, 2009 for U.S. Appl. No. 10/944,270.
USPTO Office Action dated Apr. 21, 2009 for U.S. Appl. No. 10/944,270.
USPTO Office Action dated Nov. 17, 2008 for U.S. Appl. No. 12/117,582.
USPTO Office Action dated Mar. 3, 2009 for U.S. Appl. No. 12/117,582.
USPTO Office Action dated Aug. 6, 2009 for U.S. Appl. No. 12/117,582.
USPTO Office Action dated Nov. 17, 2008 for U.S. Appl. No. 12/118,931.
USPTO Office Action dated Mar. 4, 2009 for U.S. Appl. No. 12/118,931.
USPTO Office Action dated Jul. 30, 2009 for U.S. Appl. No. 12/118,931.
USPTO Office Action dated Nov. 25, 2008 for U.S. Appl. No. 12/117,961.
USPTO Office Action dated Aug. 6, 2009 for U.S. Appl. No. 12/117,961.
USPTO Office Action dated Dec. 5, 2008 for U.S. Appl. No. 12/120,902.
USPTO Office Action dated Oct. 21, 2009 for U.S. Appl. No. 12/120,902.
USPTO Office Action dated Mar. 17, 2009 for U.S. Appl. No. 11/690,127.
USPTO Office Action dated Mar. 23, 2009 for U.S. Appl. No. 11/804,309.
USPTO Office Action dated Mar. 23, 2009 for U.S. Appl. No. 11/926,326.
USPTO Office Action dated Aug. 28, 2009 for U.S. Appl. No. 11/150,847.
U.S. Appl. No. 60/844,874, filed Sep. 15, 2006.
U.S. Appl. No. 60/922,730, filed Apr. 9, 2007.
U.S. Appl. No. 61/052,413, filed May 12, 2008.
U.S. Appl. No. 61/084,949, filed Jul. 30, 2008.
U.S. Appl. No. 11/789,705, filed Apr. 24, 2007.

\* cited by examiner

COREWIRE DESIGN AND CONSTRUCTION FOR MEDICAL DEVICES

This application is a continuation of U.S. patent application Ser. No. 13/351,774, filed Jan. 10, 2012, which is a continuation of U.S. patent application Ser. No. 12/045,308, filed Mar. 10, 2008, now U.S. Pat. No. 8,182,432, issued on May 22, 2012, the entire disclosure of such application being expressly incorporated herein by reference.

BACKGROUND OF THE INVENTION

Embodiments of the present invention relate generally to medical devices and methods and more particularly to minimally invasive devices, systems and methods for treating sinusitis and other ear, nose & throat disorders.

The human head includes a number of hollow cavities called paranasal sinuses, which connect to the nasal cavity via small openings called "ostia" (singular "ostium"). Generally, the human head includes eight paranasal sinuses (two sets of four on each side), called the frontal, ethmoid, sphenoid and maxillary sinuses. The frontal sinuses are located in the forehead, the maxillary sinuses are in the cheeks, the ethmoids are under the eyes, and the sphenoid sinuses are farther back in the head, near the pituitary gland. Paranasal sinuses are lined with mucous-producing epithelial tissue and have cilia to sweep mucous out of the sinuses and through the ostia into the nasal cavity.

Sinusitis is defined as an inflammation of the paranasal sinus lining commonly caused by bacterial, viral and/or microbial infections, as well as structural issues such as block age of the sinus ostia. Symptoms include nasal congestion, facial discomfort, nasal discharge, headache, and fatigue. Sinusitis is considered acute when symptoms last 4 weeks or less. The disease is considered chronic when it lasts 3 months or longer. Sinusitis affects 37 million people each year, making it one of the most common health problems in the U.S. It is more prevalent than arthritis and hypertension and has a greater impact on quality of life than diabetes or congestive heart failure. Sinusitis is also responsible for $8 billion in direct healthcare expenditures and a significant loss of workplace productivity.

The initial therapy typically attempted when treating chronic sinusitis is drug therapy involving anti-inflammatory agents to reduce the inflammation and antibiotics to treat the infection. A large number of patients, however, do not respond to drug therapy and seek a surgical option. The most common surgical procedure currently performed for chronic sinusitis treatment is Functional Endoscopic Sinus Surgery (FESS).

In FESS, an endoscope is inserted into the nose and, under visualization through the endoscope, the surgeon removes diseased or hypertrophic bone and soft tissue in the nasal cavity and enlarges the ostia of the effected sinuses to restore normal drainage of the sinuses. Instruments used in FESS procedures are generally rigid surgical shavers, drills and burrs, and not only are the ostia enlarged during FESS procedures, but also anatomical structures are often removed just to gain access to the ostia with the rigid surgical tools. This removal of structures increases the post-surgical pain and bleeding after FESS. FESS procedures are typically performed with the patient under general anesthesia and involve days or even weeks of recovery, with painful and uncomfortable post-surgical packing of the nasal cavity, bleeding and scarring requiring follow-up debridement procedures.

Due to the invasiveness of FESS procedures, many otolaryngologists consider FESS an option only for patients who suffer from severe sinus disease (e.g., those showing significant abnormalities under CT scan), and many patients who would benefit from a surgical solution to their chronic sinusitis nevertheless avoid surgery. Thus, patients with less severe disease may not be considered candidates for FESS and may be left with no option but drug therapy.

An alternative to FESS employs dilating balloons and related devices for less invasive sinus intervention. Examples of dilating balloons and related devices and their methods of use can be found, for example, in U.S. patent application Ser. No. 10/829,917, entitled "Devices, Systems and Methods for Treatment of Nasal and Sinus Disorders of the Ears, Nose and/or Throat" and filed on Apr. 21, 2004; Ser. No. 10/944,270, entitled "Apparatus and Methods for Dilating and Modifying Ostia for Paranasal Sinuses and Other Intranasal or Paranasal Structures" and filed on Sep. 17, 2004; Ser. No. 11/037,548, entitled "Systems and Methods for Treating Disorders of the Ear, Nose and Throat" and filed on Jan. 18, 2005; and Ser. No. 11/150,847, entitled "Devices, Systems and Methods Usable for Treating Sinusitis" and filed: Jun. 10, 2005, which are incorporated by reference in their entirety. Less invasive procedures of the type described in the above applications may sometimes be referred to as "Balloon Sinuplasty™" or more generally "Sinuplasty."

In addition to Balloon Sinuplasty™ devices, systems and methods, the assignee of the present invention has invented other devices, systems and methods for minimally invasive sinus procedures. For example, an irrigation catheter for use in the paranasal sinuses is described in U.S. patent application Ser. No. 12/011,100, entitled "Methods, Devices and Systems for Treatment and/or Diagnosis of Disorders of the Ear, Nose and Throat," and filed on Jan. 23, 2008, the full disclosure of which is hereby incorporated by reference. Another example is a lighted guidewire device for use in a Balloon Sinuplasty™ procedure, such as the embodiments described in U.S. patent application Ser. No. 11/522,497, entitled "Methods and Devices for Facilitating Visualization in a Surgical Environment," and filed Sep. 15, 2006, the full disclosure of which is hereby incorporated by reference.

In some Balloon Sinuplasty™ procedures, as well as in other procedures invented by the assignee of the present invention, such as paranasal sinus irrigation using an irrigation catheter device as described in the above-referenced patent application, a guidewire may be used for advancement and positioning of one or more devices in or through a paranasal sinus ostium and sometimes into a paranasal sinus itself. For example, in some procedures a guidewire may be advanced through an angled guide catheter, through a paranasal sinus ostium, and into a paranasal sinus. A balloon catheter may then be advanced over the guidewire to position a balloon of the catheter in the paranasal sinus ostium, and the balloon may then be inflated to expand the ostium. In some cases, the balloon catheter and guidewire may then be removed from the paranasal sinus by pulling them back through the angled guide catheter. Optionally, the same guide catheter, guidewire and balloon catheter may be used to access and expand multiple paranasal sinus ostia in one patient.

Although the assignee of the present invention has previously developed guidewires for use in such procedures, improvements are continually being sought. For example, when a distal end of a guidewire is passed into a sinus, it is often advantageous to continue to pass an additional length of guidewire into the sinus, thus causing it to curl and turn up on itself and thus facilitating confirmation of the location of the guidewire distal end in the sinus, using fluoroscopy. The distal end of the guidewire is also passed in and out of an angled guide catheter at least once and often more than once. These two parts of the procedure may often cause the guidewire to kink or bend, and this kinking or bending may make it very difficult or impossible to access subsequent paranasal sinuses in the same patient with the same guidewire. Ideally, the guidewire distal portion should be flexible enough to pass through tortuous anatomy without damaging the anatomy while also resistant to kinking and bending. The ideal guidewire should also be pushable, to allow it to be advanced through a guide catheter. Such a guidewire should also be sufficiently strong to support a balloon catheter, irrigation catheter or other device that is passed over it.

The challenges faced by a guidewire for paranasal sinus procedures are also much more daunting than those faced by a guidewire used in cardiology vascular applications. For example, the anatomy in the nasal cavity and paranasal sinuses is composed of bone covered in soft tissue, formed into many folds, twists and turns, so the sinus guidewire faces both hard tissue that it must navigate and soft tissue that it ideally will leave relatively undamaged. The circumference and shape of the paranasal sinus cavities vary significantly from patient to patient and within a patient. The circumference of a sinus cavity may vary from about 0.5 cm to about 10 cm within a patient. Based on the size of the sinus cavity, the amount of guidewire that is positioned in the sinus also can vary significantly. The amount of guidewire that is positioned in the sinus can also vary based on physician preference as well as support needed during passage of devices. The guidewire must also pass in and out of an angled guide catheter that is usually at least partially rigid while still retaining approximately it overall shape. Further, the guidewire must provide support for the balloon catheter, irrigation catheter or other device being advanced over it.

Thus, there is a need for devices and methods for easily navigating the complex anatomy of the nasal cavities and paranasal sinuses and for treating disorders of the paranasal sinuses with minimal complications due to individual variations in anatomy and causing minimal trauma to or disruption of anatomical structures that are not pathogenic. Specifically, there is a need for a guidewire that balances flexibility and ease of use with the resilience and rigidity to provide support for a balloon catheter, irrigation catheter and/or other device(s).

BRIEF SUMMARY OF THE INVENTION

Embodiments of the present invention are related to a guidewire for use in ear, nose and throat procedures. The guidewire may include an elongate core wire having a proximal region and a distal region. The distal region of the core wire may include a flattened portion adapted to provide preferential flexure along at least one axis of the wire. The distal region of the core wire may include a tip portion distal of the flattened portion, where at least one cross-sectional dimension of the tip portion is greater than at least one cross-sectional dimension of the flattened portion. The guidewire may include an outer coil disposed around at least a portion of the elongate core wire. The guidewire may also include an atraumatic tip coupled to the core wire or the outer coil.

Some embodiments of the present invention are related to a core wire for a device usable in ear, nose and throat procedures. The core wire may include a proximal portion having a first cross-sectional area and a distal tip having a second cross-sectional area. The core wire may include a transitional portion between the proximal portion and the distal tip. The transitional portion may include a third cross-sectional area, where the second cross-sectional area is greater than the third cross-sectional area.

Some embodiments of the present invention are related to a method of making a guidewire for use in ear, nose and throat procedures. In various embodiments, for example, a method for making a guidewire may include: fabricating an elongate core wire having a proximal section and a distal section; configuring a portion of the distal section to have preferential flexibility along at least one axis of the portion; configuring a distal tip portion having at least one cross sectional dimension greater than at least one cross sectional dimension of the preferentially flexible portion; and disposing an outer coil around at least part of a length of the core wire.

DETAILED DESCRIPTION OF THE INVENTION

Embodiments of the present invention are useful in sinuplasty procedures, and may also be useful in other less or minimally invasive procedures in the ear, nose, or throat. In some sinuplasty procedures, a guidewire is used to probe openings to critical structures and paranasal sinuses. After a distal end of a guidewire has been advanced into a paranasal sinus, it may sometimes be advantageous to continue advancing the guidewire, thus causing it to curl up in the sinus. A curled-up distal portion of a guidewire may facilitate, for example, viewing the distal portion via fluoroscopy, thus allowing a surgeon to confirm that the distal portion is located in the desired paranasal sinus.

A distal portion of a sinusplasty guidewire may be atraumatic and flexible (to curl and potentially straighten out upon removal), while also being at least somewhat stiff (to provide support for passing diagnostic and therapeutic devices). The distal guide wire portion may also enable or facilitate passing devices for therapeutic and diagnostic procedures by anchoring the guidewire to some degree. The distal portion of the guidewire can be low profile and small to allow easier access and crossing of narrow ostia and passageways. In certain embodiments, the distal portion of the guidewire may be resilient enough to keep its shape after multiple passes through the guide. The preferred guidewire design provides the right balance of flexibility and stiffness in the distal section to support passage of balloon catheters.

Figure 1A:
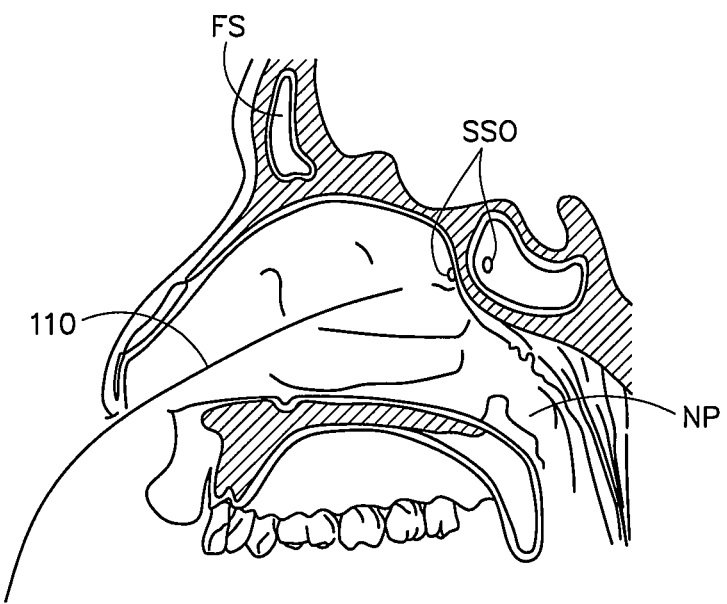
FIGS. 1A through 1D are partial sectional views through a human head showing various steps of a method for treating a paranasal sinus using a guidewire and a balloon catheter device.

Referring to FIGS. 1A-1D, in one embodiment of a Balloon Sinuplasty™ procedure, a balloon catheter is delivered over a guidewire to access, cross and dilate a sinus ostium. As shown in FIG. 1A, a guidewire 110 may be introduced into a nasal cavity. (A frontal sinus FS, sphenoid sinus, sphenoid sinus ostium SSO, and nasopharynx NP are labeled in FIGS. 1-A-1D.) To facilitate navigation through tortuous nasal cavity anatomy, guidewire 110 may have any of a number of configurations. For example, in one embodiment, guidewire 110 may be substantially straight, while in alternative embodiments it may be angled, curved or bent at a region between a proximal portion and a distal portion of guidewire 110. In many embodiments, some of which are described in the patent applications incorporated above by reference, guidewire 110 may be advanced into the nasal cavity and into a paranasal sinus through a guide catheter (not shown in FIGS. 1A-D).

Figure 1B:
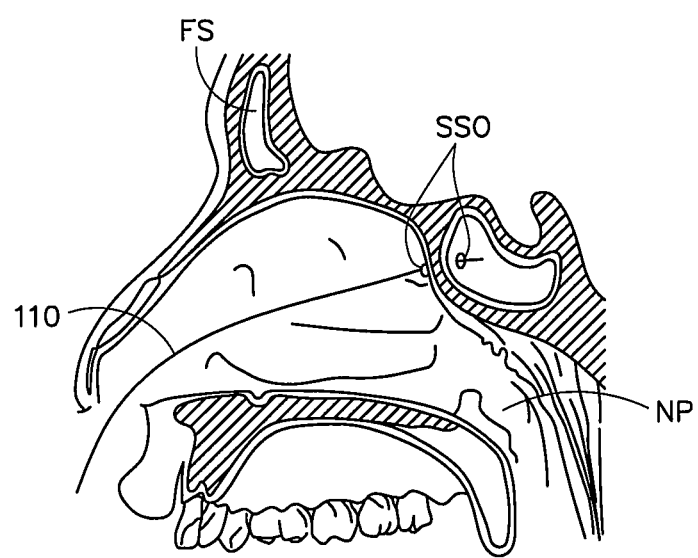
Figure 1C:
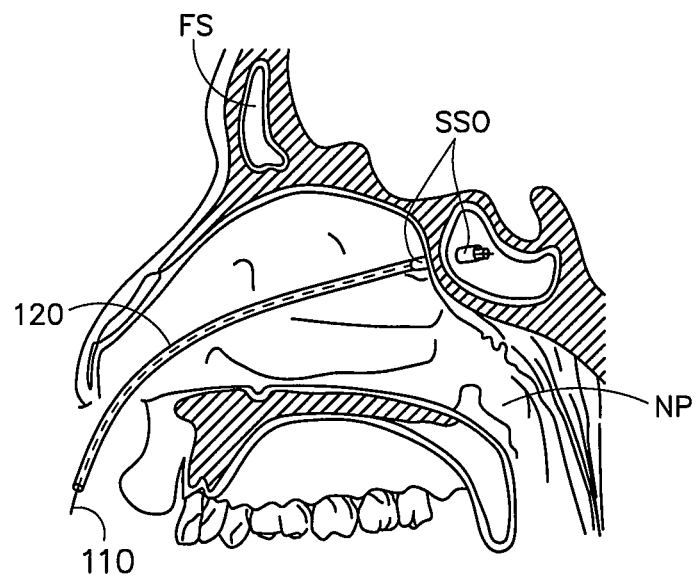
Figure 1D:
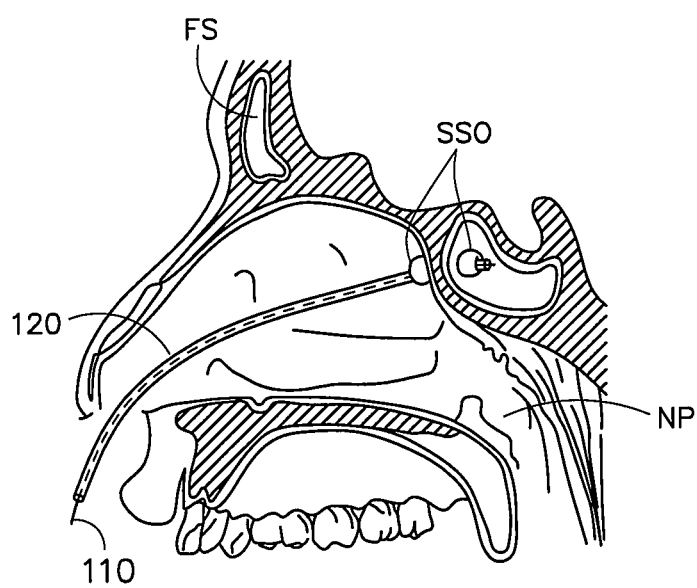

In FIG. 1B, guidewire 110 is advanced through the nasal anatomy so that the distal tip of guidewire enters a sphenoid sinus SS through an ostium SSO. In FIG. 1C, a working device in the form of a balloon catheter 120 is advanced along guidewire 110 into the sphenoid sinus SS. Typically, balloon catheter 120 will have a guidewire lumen extending through or formed in or on at least a portion of balloon catheter 120 to facilitate advancement of balloon catheter 120 over guidewire 110. The position of balloon catheter 120 is adjusted so that the balloon of the balloon catheter is located in the ostium SSO. In FIG. 1D, balloon catheter 120 is used to dilate the ostium SSO. After completion of the procedure, guidewire 110 and balloon catheter 120 are withdrawn from the nasal anatomy.

Another sinus procedure is depicted in FIGS. 2A through 2F, which are partial sectional views through a human head showing various steps of a method for accessing and treating an ethmoid sinus ES and ethmoid air cells EAC through a natural or artificially created opening of the ethmoid sinus.

Figure 2A:
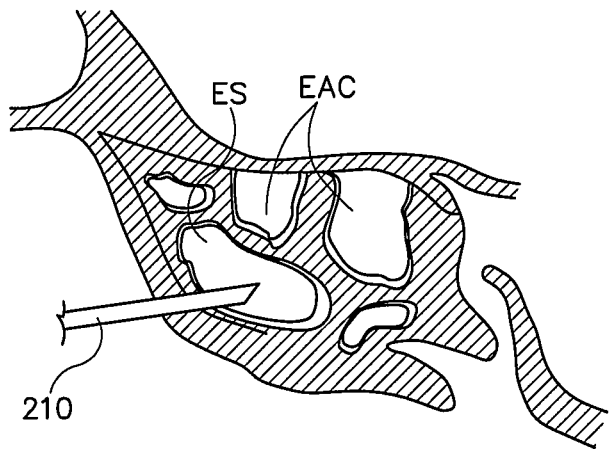
FIGS. 2A through 2F are partial sectional views through a human head showing various steps of a method for accessing and treating an ethmoid sinus through a natural or artificially created opening of the ethmoid sinus, using a guidewire and a balloon catheter device.
Figure 2B:
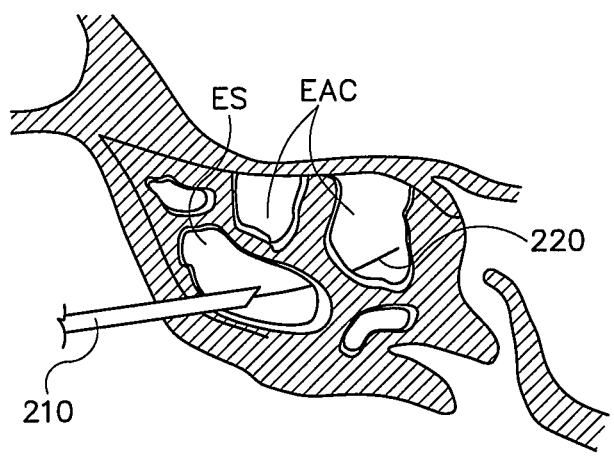
Figure 2C:
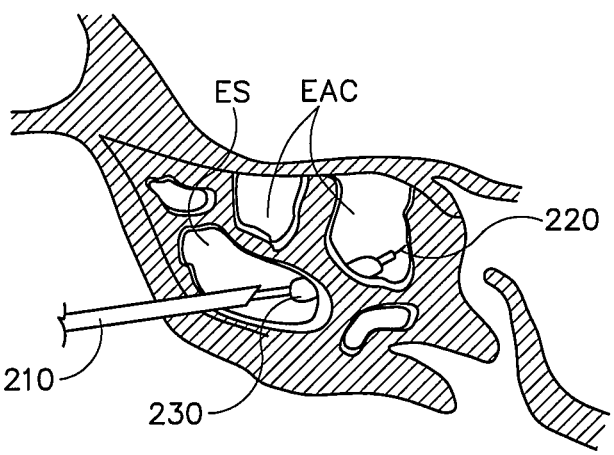
Figure 2D:
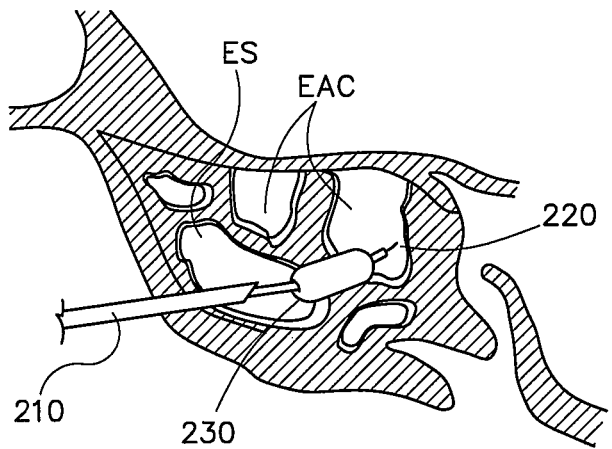
Figure 2E:
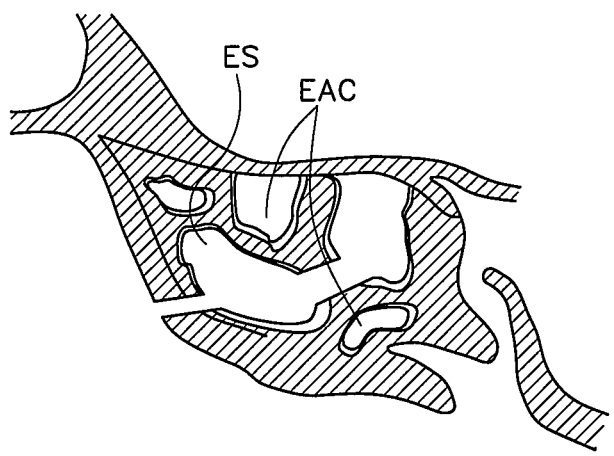

In FIG. 2A, an introducing device in the form of a guide catheter 210 is introduced in an ethmoid sinus ES. Ethmoid sinus ES comprises multiple ethmoid air cells EAC. In FIG. 2B, a guidewire 220 is introduced through guide catheter 210 into a first EAC. Thereafter, in FIG. 2C, a balloon catheter 230 is introduced over guidewire 220 into the first EAC. In FIG. 2D, balloon catheter 230 is inflated to dilate the structures of ES. In FIG. 2E, guide catheter 210, guidewire 220 and balloon catheter 230 are withdrawn leaving a first new passage in the ES. The newly created passage in the ES facilitates drainage of the mucous through the ES.

Figure 2F:
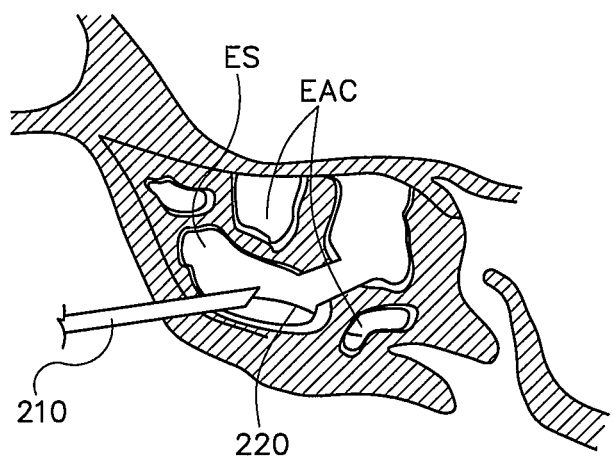

Alternatively, in FIG. 2F, only balloon catheter 230 is withdrawn. The position of guide catheter 210 is adjusted and guidewire 220 is introduced into a second EAC. A second new passage from the ES to the second EAC further facilitates drainage of the mucous through the ES. This method of dilating the structures of ES can be repeated to create multiple new passages in the ES.

Figure 3A:
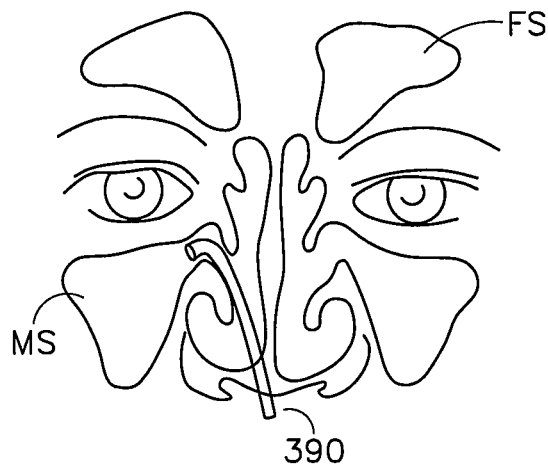
FIGS. 3A through 3C are partial sectional views through a human head showing various steps of a method of accessing a paranasal sinus using a guide catheter and a guidewire.
Figure 3B:
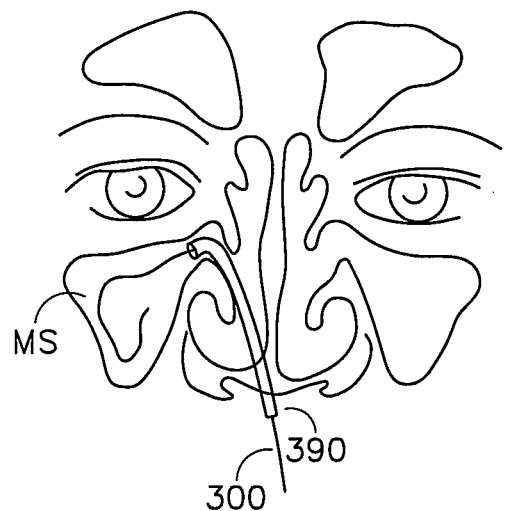
Figure 3C:
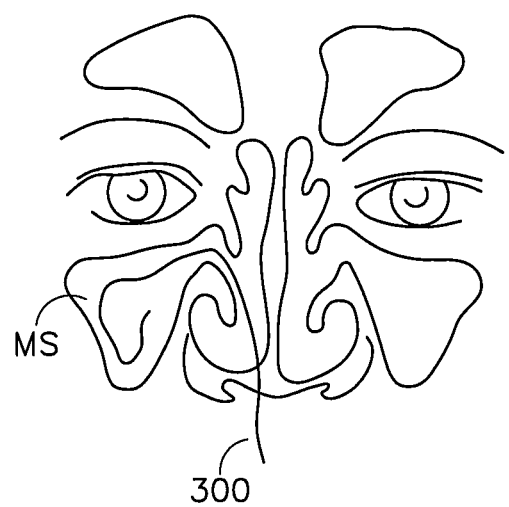

FIGS. 3A through 3C are partial sectional views through a human head showing various steps of a method of accessing a paranasal sinus using a guide catheter and a guidewire. In FIG. 3A, an angled guide catheter 390 is inserted through a nostril and placed to access a maxillary sinus MS. In FIG. 3B, guidewire 300 is advanced through guide catheter 390, around the angled bend of guide catheter 390, and into the MS. Guidewire 300 can be coiled to facilitate identification of guidewire 300 via fluoroscopy and thus verify the location of the distal portion of guidewire 300 in the MS. As shown in FIG. 3C, guide catheter 390 may then be withdrawn over guidewire 300, thus leaving guidewire 300 in place, with its distal end in the MS and its proximal end outside the patient. Any of a number of working devices, such as a balloon catheter, irrigation catheter and/or the like, can be advanced over guidewire 300 into the MS. In such a procedure, it would be advantageous for guidewire 300 to have a flexibility and stiffness profile to allow it to slide through angled guide catheter 390 and have guide catheter 390 be removed over it, multiple times, without "taking a shape" or retaining a bend or kink. It would also be advantageous for guidewire 300 to have sufficient stiffness support advancement of a balloon catheter, irrigation catheter and/or other device over it.

The foregoing three illustrated examples demonstrate some of the characteristics and properties useful for a sinuplasty guidewire, including, but not limited to:

having an atraumatic tip to allow probing of bony structures, cavities and openings;

having rigidity to access and cross a narrowed ostium or passageway and to provide support for a balloon catheter or other working device;

having flexibility and a low profile to navigate tortuous anatomy;

being steerable to allow selectively access to the desired anatomy;

having resilience to retain its shape after multiple passes through a guiding member, multiple passes through ostia, multiple curlings in sinus cavities, and multiple balloon dilations and removals;

being lubricious to allow ease of passage of working devices; and having an appropriate length to allow easier handling, improved performance, and exchange of devices.

Optimizing for one of the above properties can result in deficiencies in another property. For example, if the guidewire is too flexible, then it may become difficult to cross a tight ostium with a balloon catheter advanced over the guidewire. If the guidewire is too stiff, then it may not be easy to curl in the sinus. Also, depending on the amount of wire that curls in the sinus, the balloon support performance of the guidewire may change significantly. A useful total length of the guidewire provides ease of use and improved performance, including steerability, handling, and catheter support.

Certain other features may also be advantageous in some guidewire embodiments. For example, the proximal portion of the guidewire may be sufficiently stiff to allow translation of torque from the proximal region to the distal region, but sufficiently flexible to allow the removal of maxillary and frontal guides (which are typically more rigid than a guidewire) without losing the guidewire shape. Further, the distal portion of the guidewire that comes out of the tip of the guide catheter is not supported when accessing frontal recess or ostium. The balance of strength and flexibility is thus particularly challenging for the distal portion. The distal portion may also be radiopaque to facilitate visualization under fluoroscopy.

Figure 4A:
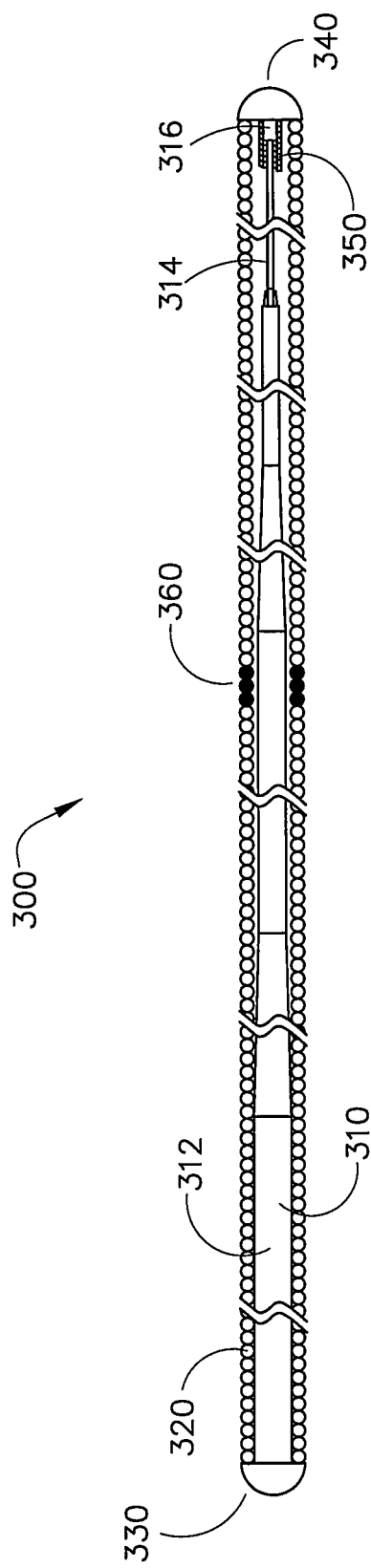
FIG. 4A illustrates a cross-sectional view of a guidewire according to one embodiment of the present invention.

FIG. 4A illustrates a view of a guidewire 300 according to certain embodiments of the present invention. Guidewire 300 includes core wire 310 and outer coil 320. While outer coil 320 encircles at least a portion of core wire 310, for ease of illustration outer coil 320 is depicted in cross section. Core wire 310 has proximal portion 312, transition portion 314, and distal portion 316. Proximal tip 330 and distal end 340 are connected to outer coil 320 and core wire 310. Outer coil 320 may also be attached to core wire 310. For example, outer coil 320 may be attached to core wire 310 along proximal portion 312. Marker coil 350 is connected to distal portion 316 and may also be connected to distal tip 340. Marker coil 350 may be alternatively or additionally connected to distal tip 340.

Still referring to FIG. 4A, proximal portion 312 of core wire 310 extends from about proximal tip 330 to transition portion 314. In certain embodiments, the length of proximal portion 312 can range from about 30 cm to about 100 cm. In certain embodiments, the length of proximal portion 312 is about 78 cm. In certain embodiments, proximal portion 312 has a generally circular cross section. In other embodiments, proximal portion 312 has a non-circular cross section. In certain embodiments, the cross section of proximal portion 312 may be generally symmetric such that its flexibility and rigidity are uniform about its long axis. While proximal portion 312 may have a generally circular cross section about substantially all of its length, the diameter of that circular cross section may vary. In certain embodiments, the diameter of the cross section of proximal portion 312 ranges from about 0.050 inches (1.27 mm) to about 0.001 inches (0.0254 mm). In certain embodiments, proximal portion 312 may have a region with a circular cross section having a diameter of about 0.019 inches (0.483 mm). Moving distally along core wire 310 from this region, proximal portion 312 may have a region with a circular cross section having a diameter of about 0.016 inches (0.406 mm). In between these two regions of differing diameters, proximal portion 312 may have a tapered region whose diameter varies from about 0.019 inches (0.483 mm) to about 0.016 inches (0.406 mm). The diameter of the tapered region may vary linearly or non-linearly along its length. In certain embodiments, proximal portion 312 has multiple regions of constant diameter cross section connected by multiple tapered regions. Generally, the diameter of the cross section of proximal portion 312 decreases in the distal direction. In certain embodiments, the region of proximal portion 312 that is immediately proximal of transition portion 314 has the smallest diameter cross section of any region of proximal portion 312. In certain embodiments, this distal-most region of proximal portion 312 has a cross section with a diameter of about 0.0065 inches (0.165 mm).

Referring still to FIG. 4A, core wire 310 includes distal portion 316. Distal portion 316 extends from about distal tip 340 to transition portion 314. In certain embodiments, the length of distal portion 316 ranges from about 0.2 cm to about 2.0 cm. In certain embodiments, the length of distal portion 316 is about 0.5 cm. In certain embodiments, distal portion 316 has a generally circular cross section. In other embodiments, distal portion 316 has a non-circular cross section. In certain embodiments, the cross section of distal portion 316 may be generally symmetric such that its flexibility and rigidity are uniform about its long axis. The diameter of the cross section of distal portion 316 may be generally constant along its length or the diameter may vary. In certain embodiments, the diameter of the cross section of distal portion 316 ranges from about 0.050 inches to about 0.001 inches. In certain embodiments, the diameter of the cross section of distal portion 316 is about 0.007 inches (0.178 mm) along substantially all of its length.

Referring still to FIG. 4A, transition portion 314 extends from proximal portion 312 to distal portion 316. In certain embodiments, the length of transition portion 314 ranges from about 0.5 cm to about 5.0 cm. In certain embodiments, the length of distal portion 316 is about 0.5 cm. The transition portion, and in particular the cross section of the transition portion, is discussed in more detail below in reference to FIGS. 5A and 5B.

Referring again to FIG. 4A, outer coil 320 is disposed around core wire 310. In certain embodiments, outer coil 320 extends substantially the entire length of core wire 310. In some embodiments, outer coil 320 is shorter than core wire 310, and in other embodiments outer coil 320 is longer than core wire 310. In certain embodiments, the wire forming outer coil 320 may have a circular cross section, as shown in FIG. 4A. In other embodiments, the wire forming outer coil 320 may have a non-circular cross section, such as a rectangular cross section. In certain embodiments, the pitch of outer coil 320 is closed, such that there is substantially no space between coils. In certain embodiments, the pitch of outer coil 320 is open, such that there is space between coils. In certain embodiments, outer coil 320 has regions of both closed and open pitch. Open pitch coils tend to be more flexible than closed pitch coils while closed pitch coils tend to have better pushability than open pitch coils. It may be advantageous to vary the flexibility of one section of outer coil 320 as compared to another section.

Still referring to FIG. 4A, depth marker 360 is a region of outer coil 320 that is visually distinct from the rest of outer coil 320. Depth marker 360 may be an etched or colored region of outer coil 320. Depth marker 360 allows a physician to determine how much of the guidewire is inside a patient's anatomy. In certain embodiments, the length of depth marker 360 ranges from about 3 mm to about 15 mm. In certain embodiments, the length of depth marker 360 is about 9 mm.

Referring again to FIG. 4A, proximal tip 330 is connected to outer coil 320 and core wire 310. In certain embodiments, proximal tip 330 has a rounded surface for ease of handling. Distal tip 340 is also connected to outer coil 320 and core wire 310. In certain embodiments, distal tip 340 has a rounded surface to provide an atraumatic tip for minimizing damage to tissue during guidewire use.

Figure 4B:
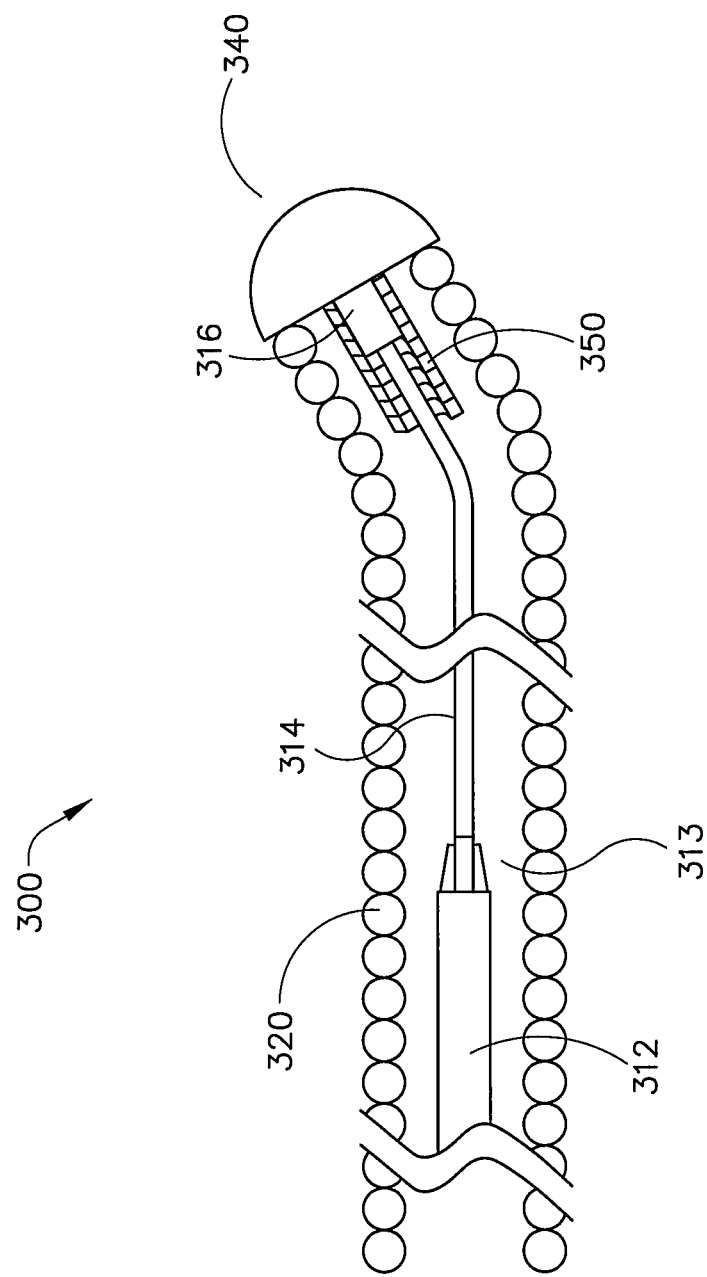
FIG. 4B illustrates a close-up view of a distal region of the guidewire of FIG. 4A.

FIG. 4B illustrates a close-up view of the distal region of guidewire 300. In the embodiment illustrated in FIG. 4B, the distal region of guidewire 300 has been pre-shaped to include a bend and further includes radiopaque marker 350. In certain embodiments, the angle of the bend ranges from about 1 degree to about 135 degrees. In certain embodiments, the angle of the bend ranges from about 15 degrees to about 30 degrees. In some embodiments, the angle of the bends can be about 30 degrees, about 45 degrees, about 60 degrees, about 70 degrees, about 90 degrees, or about 120 degrees. The distal tip may be preshaped or it may be shaped by the user.

Still referring to FIG. 4B, radiopaque marker 350 is connected to distal tip 340. In certain embodiments, radiopaque marker 350 is connected to distal portion 316. In certain embodiments, radiopaque marker 350 is connected to transition portion 314. In certain embodiments, radiopaque marker 350 is connected to outer coil 320. Radiopaque marker 350 may be a coil, as in the embodiment depicted in FIG. 4B, or it may be another shape. In certain embodiments, the length of radiopaque marker 350 ranges from about 0.2 cm to about 2 cm. In certain embodiments, the length of radiopaque marker 350 is about 0.5 cm.

Figure 5A:
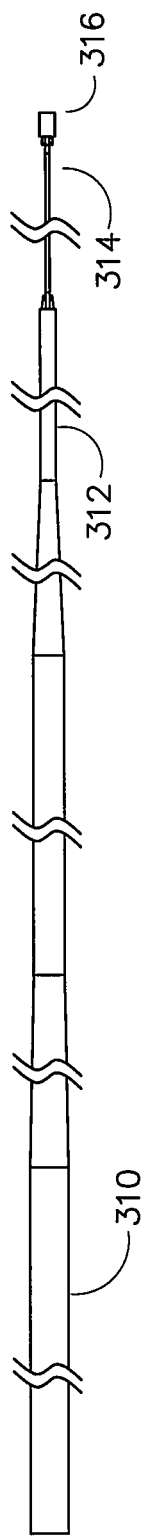
FIGS. 5A and 5B illustrate two views of a core wire according to one embodiment of the present invention.
Figure 5B:
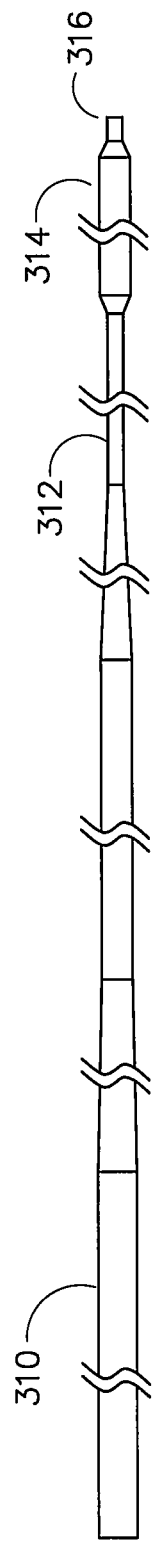

FIGS. 5A and 5B illustrate two views of a core wire 310 according to one embodiment. The perspective of FIG. 5A is 90 degrees different from the perspective of FIG. 5B. In these complementary views, the shape of transition portion 314 is more easily appreciated. FIG. 5A is a similar perspective to FIG. 4B. From FIG. 5B, it is apparent that transition portion 314 has flattened profile. In certain embodiments, transition portion 314 has a generally rectangular cross section. In certain embodiments, transition portion has a generally elliptical cross section. Typically, the width of transition portion 314 (the width is the dimension depicted in FIG. 5B, for example) is greater than the thickness of transition portion 314 (the thickness is the dimension depicted in FIG. 5B, for example). In certain embodiments, the width of transition portion 314 can range from about 0.002 inches (0.051 mm) to about 0.1 inches (2.54 mm). In certain embodiments, the width of transition portion 314 is about 0.01 inches (0.254 mm). In certain embodiments, the thickness of transition portion 314 can range from about 0.001 inches (0.0254 mm) to about 0.08 inches (2.032 mm). In certain embodiments, the thickness of transition portion 314 is about 0.0035 inches (0.0889 mm).

Referring still to FIGS. 5A and 5B, the flattened cross section of transition portion 314 provides certain advantageous mechanical properties. For example, transition portion 314 will bend more easily in its thickness dimension than in its width dimension. This type of bending is depicted, for example, in FIG. 4B. In contrast, proximal portion 312 does not have a preferential bending direction, in certain embodiment of the invention where proximal portion 312 has a circular or other symmetrically shaped cross section. Generally, a wire flexes and creates and angle with its long axis. This axis of flexion is generally independent of wire orientation when the wire has a symmetric cross section. In certain embodiments where transition portion 314 has a flattened cross section, transition portion 314 is more flexible along one axis of flexion than another. Preferential flexibility is useful in a sinuplasty guidewire, for example, to facilitate guidewire steering.

In certain embodiments, the cross sections of the different portions of the core wire are arranged in specific relationships in order to provide the appropriate balance of properties for use in a sinuplasty guidewire. In certain embodiments, the cross sectional area of a distal portion of the core wire is greater than the cross sectional area of the transition portion of the core wire. In such embodiments, the distal portion may have sufficient resilience and rigidity to probe sinus cavities and bony structures while the transition portion may be flexible and steerable. In certain embodiments, the cross sectional area of a distal portion of the core wire is greater than the cross sectional area of a proximal portion of the core wire. In such embodiments, the distal portion may have sufficient resilience and rigidity while the proximal portion may be flexible and steerable. In certain embodiments, the diameter of the cross section of a distal portion of the core wire is greater than the thickness of the cross section of the transition portion of the core wire. In certain embodiments, the diameter of the cross section of a distal portion of the core wire is at least twice the thickness of the cross section of the transition portion of the core wire.

Guidewires of certain embodiments have different amounts of flexibility in different regions. For example, a proximal region of guidewire (extending from the proximal end of the guidewire to a point ranging from about 15 cm to about 88 cm distal of the proximal end) may have a stiffness ranging from about 6000 mg force (Gurley units) to about 18,000 mg force. Continuing this example, a mid section of the guidewire (extending about 10 cm distally from the distal end of the aforementioned proximal section) may have a stiffness ranging from about 2400 mg force to about 2800 mg force. Continuing this example, a distal section of the guidewire (the final section of the guidewire, about 2 cm in this example) may have a stiffness ranging from about 200 mg force to about 400 mg force. In this example, the guidewire has a balance of flexibility and rigidity.

Referring now again to FIG. 4B, and keeping in mind the flattened cross section of certain embodiments of transition portion 314, proximal portion 312 is connected to transition portion 314 via proximal transition taper 313. Further, transition portion 314 is connected to distal portion 316 via distal transition taper 315. The cross sections of proximal transition taper 313 and distal transition taper 315 may be, independently, flattened or symmetric.

Guidewires and their constituent parts for use according to embodiments the present invention may be manufactured as follows. Core wire 310 can be formed by any known wire-forming process, such as drawing. Any conventional wire material may be suitable for forming core wire 310. However, certain embodiments may use materials generally known for their use in medical devices, such as alloys of stainless steel and alloys of nickel and titanium (conventionally known as nitinol or NiTi). In certain embodiments, core wire 310 is formed from a nickel-titanium alloy. The profile of the cross section of a region of core wire 310 may be formed by the choice of draw plate in the drawing process, or it may be formed by a grinding or other shaping process after the wire is drawn. Similarly, the different diameters and the tapered regions of core wire 310 may be formed by further reducing the diameter of those regions using a staged drawing technique or by a material removal technique, such as grinding. Also, transition portion 314 may be formed by drawing techniques or material removal techniques. Further, transition portion 314 may be formed by a flattening, rolling, or stamping_technique (or an equivalent technique). Conventional metal working techniques, such as cold working or heat treatment, may also be used to impart useful properties to core wire 310. For example, the austenite finish temperature of the nitinol alloy used to form the core wire may be controlled to impart a desired flexibility and resilience.

Outer coil 320 may also be formed from any conventionally known wire forming material. Certain embodiments may use materials generally known for their use in medical devices, such as alloys of stainless steel, alloys of nickel and titanium, platinum and the like. In certain embodiments, outer coil 320 is formed from a stainless steel alloy. Outer coil 320 may be formed from a round wire, a flat wire, or a wire of any other cross section. In certain embodiments, outer coil 320 is formed by wrapping wire around a mandrel to form a coil. The coil can then be removed from the mandrel and placed coaxially with a core wire. Alternatively, outer coil 320 can be formed by wrapping a wire directly around a core wire such that the core wire acts as the mandrel for forming the coil.

Radiopaque marker 350 may be formed from any conventionally known radiopaque materials, including iridium, platinum, tungsten, gold or alloys thereof. In certain embodiments, radiopaque marker 350 is formed from an alloy of 92% platinum and 8% tungsten. Radiopaque marker 350 may be formed into a coil by wrapping around a mandrel (including using the core wire as a mandrel). In certain embodiments, radiopaque marker 350 may be placed around core wire 310. In certain embodiments, radiopaque marker 350 is a coil with the same inner diameter and pitch as a region of outer coil 320. In such embodiments, radiopaque coil 350 may be placed such that the coils of outer coil 320 alternate with the coils of radiopaque marker 350. In some embodiments, radiopaque marker 350 is not a coil, but a tab of material that can be attached to another component of the guidewire. In certain embodiments, a region of outer coil 320 may itself be formed of radiopaque material.

Components of the guidewire may be connected with one another by any suitable method, including welding, soldering, brazing, swaging, adhesives, laser bonding, compression fitting, or combinations thereof. In certain embodiments, the proximal and distal ends of the guidewire are connected using solder that forms the proximal tip 330 and the distal tip 340. In such embodiments, a plug of solder is brought into contact with the end of the guidewire and the region is heated to cause the solder flow. The final shape of the tip can be controlled and formed into a rounded, atraumatic shape. In other embodiments, proximal tip 330 and, independently, distal tip 340 can be formed from rounded components that are attached to the ends of the guidewire. These tip components can be formed of any suitable material.

Lubricious coatings may be applied to any of the parts of guidewire 300. Such coatings are intended to reduce friction. Core wire 310 may have a lubricious coating, for example, to reduce the friction between it and the inner surface of outer coil 320. Similarly, the inner surface of outer coil 320 may have a lubricious coating to reduce the friction between it and core wire 310. The outer surface of outer coil 320 may have a lubricious coating to reduce the friction between it and tissue. Lubricious coatings may be formed from any suitable material, including polymers, such as PTFE, and hydrogels conventionally used in medical devices as lubricious coatings. In certain embodiments, the lubricious coating is formed of silicone polymer.

Guidewires made according to embodiments of the present invention can be used in sinusplasty procedures. Specifically, such guidewires can be used to locate the desired sinus anatomy and provide support for a dilating member or other treatment device because such guidewires achieve the appropriate balance of flexibility, rigidity, steerability, resilience, and support. In particular, such guidewires are useful because, as compared to guidewires typically used in the vasculature, they can provide support for a dilating member with less reliance on the patient's anatomy to assist in supporting the dilating member.

EXAMPLE

In one example, the stiffness of a guidewire designed and constructed according to an embodiment of the present invention was compared to a standard sinuplasty guidewire and a "floppy" sinusplasty guidewire.

An 80 cm guidewire with the following dimensions was tested in a standard guidewire flexibility test (STM02236):
Core wire (nickel titanium)
$1^{st}$ proximal region—length 55.8 cm; diameter 0.019 inches
$1^{st}$ taper region—length 3.5 cm
$2^{nd}$ proximal region (mid region)—length 14.5 cm; diameter 0.016 inches
$2^{nd}$ taper region—length 3.2 cm
$3^{rd}$ proximal region—length 1.5 cm; diameter 0.0065 inches
transition region—length 1.1 cm; thickness 0.0035 inches; width 0.01 inches
distal region—length 0.2 cm; diameter 0.007
outer coil (stainless steel)
formed of 0.007 inch wire to 0.033 inch coil; length 80 cm
radiopaque coil (92% platinum/8% tungsten)
0.016 inch diameter coil; length 0.5 cm
proximal and distal tips
smooth solder caps The stiffness of 10 samples of such a guidewire was compared at the distal region (final 3 cm) and at the balloon support region (distal 10 cm). The results are presented in Table 1 below:

TABLE 1

Stiffness Comparison (mg Force)

|  | Distal region (Ave) | Support Region (Ave) |
|---|---|---|
| Test GW | 2582.9 | 431.6 |
| Standard GW | 3227.4 | 461.1 |
| Floppy GW | 1227.7 | 344.1 |

The test guidewire provides about 20% less balloon support than standard guidewire and about 50% more than the floppy guidewire. The test guidewire provides comparable distal flexibility as compared to the standard guidewire.

While the invention has been described with reference to certain embodiments, various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A method for positioning a working device at a desired location within a human or animal subject, the method comprising:
  (a) inserting a guidewire into a nostril of the subject, the guidewire comprising:
    (i) a core wire, comprising:
      (A) a proximal portion comprising a distal end and a proximal tip,
      (B) a cylindraceous distal tip, and
      (C) a single, continuous flattened portion having a first end and a second end, wherein the flattened portion includes a uniform cross section, wherein the first end of the flattened portion contacts the distal end of the proximal portion, wherein the second end of the flattened portion contacts the distal tip, wherein the flattened configuration imparts resilience to at least the distal tip, wherein the flattened portion is wider than the proximal portion, when viewed from at least one view, and
    (ii) a flexible outer member surrounding at least a portion of the core wire, wherein the outer member comprises a distal end, wherein the distal end of the outer member includes an atraumatic tip, wherein at least the core wire comprises a preformed bend at the flattened portion thereof; and
  (b) directing the guidewire further into the nostril such that the distal tip is adjacent to a target structure;
  (c) inserting a balloon catheter comprising an expandable balloon over the guidewire such that the expandable balloon is adjacent to the target structure; and
  (d) expanding the expandable balloon to thereby dilate the target structure.

2. The method according to claim 1, wherein the target structure is a sinus ostium.

3. The method according to claim 1, wherein the core wire comprises a preformed bend at a distal portion thereof, wherein the preformed bend is formed at an angle corresponding to accessing the target structure.

4. The method according to claim 1, further comprising inserting a guide device with the guidewire prior to inserting the balloon catheter over the guidewire, wherein inserting the balloon catheter over the guidewire comprises inserting the balloon catheter through a lumen of the guide device.

\* \* \* \* \*